United States Patent
Nijlunsing et al.

(10) Patent No.: US 11,198,006 B1
(45) Date of Patent: Dec. 14, 2021

(54) EFFICIENCY IN WIRELESS ENERGY CONTROL FOR AN IMPLANTABLE DEVICE

(71) Applicant: Salvia BioElectronics B.V., Eindhoven (NL)

(72) Inventors: Rutger Nijlunsing, Eindhoven (NL); Hubert Martens, Eindhoven (NL)

(73) Assignee: SALVIA BIOELECTRONICS B.V., Eindhoven (NL)

( * ) Notice: Subject to any disclaimer, the term of this patent is extended or adjusted under 35 U.S.C. 154(b) by 0 days.

(21) Appl. No.: 17/220,841

(22) Filed: Apr. 1, 2021

(51) Int. Cl.
  *A61N 1/36* (2006.01)
  *A61N 1/14* (2006.01)
  *G16H 40/63* (2018.01)
  *A61N 1/372* (2006.01)

(52) U.S. Cl.
  CPC ........... *A61N 1/36175* (2013.01); *A61N 1/14* (2013.01); *A61N 1/36003* (2013.01); *A61N 1/36062* (2017.08); *A61N 1/36071* (2013.01); *A61N 1/36192* (2013.01); *A61N 1/36196* (2013.01); *A61N 1/37252* (2013.01); *G16H 40/63* (2018.01)

(58) Field of Classification Search
  CPC .................. A61N 1/36175; A61N 1/36062
  See application file for complete search history.

(56) References Cited

U.S. PATENT DOCUMENTS

| | | | | |
|---|---|---|---|---|
| 2004/0210289 A1* | 10/2004 | Wang | ...................... | A61N 1/05 607/116 |
| 2005/0004619 A1* | 1/2005 | Wahlstrand | .......... | A61N 1/3787 607/45 |
| 2005/0288739 A1* | 12/2005 | Hassler, Jr. | .......... | A61N 1/3787 607/61 |
| 2007/0191888 A1* | 8/2007 | Wang | .................... | A61N 1/3787 607/2 |
| 2009/0216296 A1* | 8/2009 | Meskens | ............... | A61N 1/3787 607/57 |
| 2010/0114205 A1* | 5/2010 | Donofrio | ................. | A61N 1/37 607/4 |
| 2012/0310316 A1* | 12/2012 | Janik | ........................ | A61N 1/05 607/116 |
| 2018/0085593 A1* | 3/2018 | Fayram | ................. | A61N 1/3787 |
| 2020/0188675 A1* | 6/2020 | Marceglia | .......... | A61N 1/36175 |

* cited by examiner

*Primary Examiner* — William J Levicky
(74) *Attorney, Agent, or Firm* — Fresh IP PLC; Clifford D. Hyra; Aubrey Y Chen

(57) ABSTRACT

During charging of implantable devices via inductive coupling, heat may be produced within the implantable device, so control of the charging may be desirable to reduce or avoid the risk of undesirable tissue heating. Exchanging parameters relevant for charging may prevent undesirable heating, but typically increase the complexity of the devices used.

An implantable device is provided, for wirelessly receiving energy pulses, monitoring the energy storage, and transmitting a first sufficient energy signal if the energy storage exceeds a first maximum value. An associated energy transmission device is provided, for wirelessly transmitting a plurality of successive energy pulses transmitted at a first power level, pausing energy transmission immediately after the first sufficient energy signal is received, and subsequently resuming energy pulse transmission at the first power level if no further sufficient energy signal is received.

33 Claims, 10 Drawing Sheets

EFFICIENCY IN WIRELESS ENERGY CONTROL FOR AN IMPLANTABLE DEVICE

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

TECHNICAL FIELD

The present disclosure relates to an improved method of controlling wireless energy transfer from an energy transmission device to a wireless implantable device. It further relates to an improved energy controller for a wireless implantable device. In particular, it relates to an improved energy controller for a wireless implantable stimulator for providing electrical stimulation to human or animal tissue, having an electrode array located along a substrate.

BACKGROUND

Implantable devices may be used to monitor a condition. Additionally or alternatively, they may deliver treatment for therapeutic or cosmetic reasons. In many long term or chronic uses, implantable devices now include a rechargeable energy source (e.g., comprising one or more capacitors or batteries) to maintain or even extend the operational life. In general, it is also desirable to optimize the time between recharging, so that the device may operate correctly during treatment. For implantable stimulators, configured and arranged to provide electrical stimulation as treatment, the optimization may be more important to increase the chances of correct treatment.

In many cases, the charging device is external, providing transcutaneous charging. In some examples, charging may be performed via inductive coupling between a primary coil in the charging device and a secondary coil in the implantable device. When a current is applied to the primary coil and the primary coil is aligned to the secondary coil, electrical current is induced in the secondary coil for charging. During charging, heat may be produced within the implantable device, so the charging is controlled to reduce or avoid the risk of undesirable tissue heating. For example, the charging energy and/or duration and/or interval may be controlled.

More recently, implantable devices have appeared with a charging coil for charging the implantable device, and also for communicating in either one or both directions. Parameters relating to the charging of the implantable device may thus be directly provided to the charging device, allowing a more accurate reduction and/or avoidance of undesirable heating.

Although this allows a more complex control of charging, there is also a need for improving the charging control, in particular, for implantable devices that do not have a battery, to allow for miniaturized and safe designs.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description. Rather, the scope of the invention is defined by the appended claims.

In certain embodiments, the disclosed embodiments may include one or more of the features described herein.

Although the method of wireless energy control is described for an implantable device, the disclosure may also be implemented without requiring any potentially surgical step.

A method of controlling wireless energy transfer from an energy transmission device to a wireless implantable device is provided, the implantable device comprising: one or more energy receivers, configured and arranged to wirelessly receive a plurality of successive energy pulses, transmitted at a first power level; an energy storage, configured and arranged to store at least a portion of the energy received by the one or more energy receivers; an energy monitor, configured and arranged to monitor a status level of the energy storage, wherein the status level is significantly affected by energy received by the implantable device and/or energy used by the implantable device; the energy transmission device comprising: one or more energy transmitters, configured and arranged to wirelessly transmit a plurality of energy pulses at the first power level; one or more signal receivers, configured to detect sufficient energy signals from the implantable device; the method comprising: the energy transmission device starting energy pulse transmission at the first power level; the energy transmission device and the implantable device creating an energy transmission channel between the one or more energy transmitters and the one or more energy receivers; the implantable device transmitting a first sufficient energy signal if the status level of energy storage exceeds a first maximum value; the energy transmission device pausing energy pulse transmission immediately after the first sufficient energy signal is received; and subsequently resuming energy pulse transmission at the first power level if no further sufficient energy signal is received.

This reduces the risk that the temperature of the implantable device becomes undesirably high by mainly transmitting energy when needed using a relatively simple status signal.

In particular, remedial actions are triggered by a similar, sometimes identical, signal from the implantable device. Generation of such a feedback signal may only utilize simpler electronics, further reducing the required complexity of the implantable device. A fixed power transmitter may be used, reducing complexity of the external transmission device. Remedial actions performed by the external power transmitter are similar, sometimes identical—pausing transmission of the energy pulses as soon as possible.

In addition, energy transfer control may be performed with limited or even no handshaking protocols. Especially for medical implants, it is advantageous that the implantable device has a high degree of independence from external devices for correct operation. Also, little or no handshaking may reduce the communication overhead, further increasing the speed of response by the external transmission device.

Optionally, the method comprises the energy transmission device pausing energy pulse transmission within 2 milliseconds or less, within 1 millisecond or less, within 100 microseconds or less, or within 10 microseconds or less, after the first or further sufficient energy signal is received.

Although additional features and functions may also be implemented, the relatively simple control of energy transfer allows a relatively quick decision-making. It may be advantageous to predetermine and/or control the stopping time to be as small as possible as this reduces the risk that the implantable device receives too much energy.

Additionally or alternatively, the energy storage is configured and arranged to provide sufficient energy to operate the implantable device, whereby the duration of the pause in energy pulse transmission is 1000 ms (milliseconds) or less, 500 ms or less, 200 ms or less, 100 ms or less, 50 ms or less, 20 ms or less, or 10 ms or less.

Minimizing the time that the implantable device may operate without receiving external energy may reduce the complexity of the implantable device (and thus the cost), it may reduce the amount of energy stored (and thus the risk of overheating), and it may further reduce "charging times" when energy is being stored (and thus also the risk of overheating during "charging").

Optionally, the method further comprises: predetermining and/or controlling the energy transmission device to transmit energy pulses with a first duration; the energy transmission device starting the transmission of a first pulse with the first duration; the energy transmission device receiving the first or further sufficient energy signal and the energy transmission device pausing energy pulse transmission, whereby the first pulse is truncated, and the truncated duration is less than the first duration.

By allowing the energy transmission to be paused by truncating the current pulse (if applicable), the risk of overheating may be further reduced.

Optionally, the method comprises: the implantable device transmitting the first and/or further sufficient energy signal by modifying one or more parameters of the energy transmission channel, whereby the modification of the one or more parameters is detectable by the energy transmission device.

By using the existing energy transmission channel for providing the sufficient energy signal, complexity may be further reduced as a dedicated communication channel is not required.

For example, the implantable device may modify the tuning of the energy transmission channel to transmit as load-shift keying (LSK).

Optionally, the energy transmission device: monitors one or more historic parameters associated with one or more transmitted energy pulses; monitors the one or more historic parameters before the first and/or further sufficient energy signal are received; generates a monitor dataset comprising one or more historic parameters; generates a history database comprising a plurality of monitor datasets; derives, from the history database, an expected amount of energy to be transmitted before a sufficient energy signal is received; compares a subsequent monitor dataset with the expected amount of energy to be transmitted; and identifies a significant difference between the expected amount of energy to be transmitted and the subsequent monitor dataset.

This may be advantageous as one or more significant differences may indicate that the status of the implantable device has changed, or is predicted to change—for example, that the implantable device is defective, that a risk of defective operation is increased, that a risk of inefficient operation is increased, that an unexpected degree of ingress of fluid has occurred, that a primary and/or secondary energy source has an unwanted degree of depletion, or any combination thereof.

Optionally, the implantable device: provides a degree of detuning of the energy transmission channel if the energy storage status level exceeds a second maximum value. This may allow a direct control of the detuning and the quality of the energy transfer.

Optionally, the implantable device further comprises one or more voltage regulators controlling at least a portion of the energy stored in the energy storage, the method further comprising: the implantable device reducing the output voltage of the voltage regulator if the energy storage status level exceeds a third maximum value.

This may be advantageous as it provides an automatic protection against very high voltages. In practice, the third level may determine the maximum energy storage possible within the implantable device.

Optionally, the implantable device further comprises one or more shunts for reducing at least a portion of the energy stored in the energy storage, the method further comprising: the implantable device operating the one or more shunts if the energy storage status level exceeds a third maximum value.

This may be advantageous as shunts, such as Zener diodes, may provide a relatively reliable, automatic and simple protection against very high voltages.

Optionally, the implantable device may be configured and arranged: to transmit sufficient energy signals centered around two or more modulation frequencies; and to select the central modulation frequency of the first and/or further sufficient energy signals.

A suitable energy transmission device comprises one or more signal receivers, configured to detect two or more center modulation frequencies of the first and/or further sufficient energy signals.

This may be advantageous as the further communication channel may be less sensitive to the Q-factor (or Quality factor) of the energy transmission channel.

It may be advantageous wherein the implantable device is configured and arranged to transmit sufficient energy signals centered around two modulation frequencies as this allows a binary encoding to be used. Any frequencies may be used, including modulation frequencies centered around approximately 212 kHz and approximately 424 kHz.

In general, it may be advantageous to simplify the additional data and/or information being sent using modified sufficient energy signals to reduce the risk of distorting or delaying the primary request to pause transmission.

Optionally, the energy transmission device may be configured and arranged to modify one or more parameters of the energy pulse transmission based on one or more center modulation frequencies of the first and/or further sufficient energy signals.

Optionally, the one or more parameters may include: a default transmission pulse duration; a pause duration until the next transmission pulse should be sent, a default power level of a plurality of energy transmission pulses, feedback regarding a quality of energy transfer, feedback regarding a quality of any data transmission from the energy transmission device, an energy storage status, an indication of health of the implantable device, measurement data, or any combination thereof.

When configured and arranged as an implantable stimulator, the implantable device may further comprise: a pulse generator, configured and arranged to receive electrical energy from the energy storage for its operation, and further configured to generate at least one stimulation pulse; at least two electrodes; and a plurality of electrical interconnections, electrically coupling the pulse generator to the at least two electrodes; the method further comprising: configuring and arranging the pulse generator to provide electrical stimulation energy to the at least two electrodes as one or more electrical treatment stimulation pulses.

The features may be particularly advantageous when implemented in an implantable stimulator because these typically require a more complex control of energy, and power usage may be high during use.

Optionally, the at least two electrodes may be configurable, using one or more parameters of the pulse generator, as a stimulation electrode, or a return electrode.

Optionally, the pulse generator may comprise the one or more energy receivers.

Optionally, the implantable device configured and arranged as an implantable stimulator may further comprise: a substrate, the substrate comprising a first and second surface, wherein a thickness of the substrate is defined by the first and second surfaces; wherein: the at least two electrodes are comprised in an electrode array, located along a conformable portion of the substrate; wherein the plurality of electrical interconnections are positioned between the first and second surfaces of the substrate; and wherein the thickness of the substrate along the conformable portion is equal to or less than 0.5 millimeters.

Optionally, the conformable portion of the substrate may comprise a polymer and/or a Liquid Crystal Polymer (LCP).

Optionally, the substrate comprises a further portion along which the pulse generator is located, the implantable device further comprising an encapsulation layer at least partially covering the further portion of the substrate.

In general, an implantable device, suitable for performing the methods (as disclosed herein) of controlling wireless energy transfer from an energy transmission device, comprises: one or more energy receivers, configured and arranged to wirelessly receive a plurality of successive energy pulses, transmitted at a first power level; an energy storage, configured and arranged to store at least a portion of the energy received by the one or more energy receivers; an energy monitor, configured and arranged to monitor a status level of the energy storage, wherein the status level is significantly affected by energy received by the implantable device and/or energy used by the implantable device; the implantable device being further configured and arranged: to create an energy transmission channel between the one or more energy receivers and one or more energy transmitters comprised in the energy transmission device; and to transmit a first sufficient energy signal if the status level of energy storage exceeds a first maximum value.

In general, an energy transmission device, suitable for performing the methods (as disclosed herein) of controlling wireless energy transfer to a wireless implantable device, comprises: one or more energy transmitters, configured and arranged to wirelessly transmit a plurality of energy pulses at the first power level; and one or more signal receivers configured to detect sufficient energy signals from the implantable device; the energy transmission device being further configured and arranged: to create an energy transmission channel between the one or more energy transmitters and one or more energy receivers comprised in the wireless implantable device; to pause energy pulse transmission immediately after the first sufficient energy signal is received; and to subsequently resume energy pulse transmission at the first power level if no further sufficient energy signal is received.

BRIEF DESCRIPTION OF THE DRAWINGS

Certain illustrative embodiments illustrating organization and method of operation, together with objects and advantages may be best understood by reference to the detailed description that follows, taken in conjunction with the accompanying drawings, which are not necessarily drawn to scale.

The accompanying drawings, which are incorporated herein and form a part of the specification, illustrate exemplary embodiments and, together with the description, further serve to enable a person skilled in the pertinent art to make and use these embodiments and others that will be apparent to those skilled in the art.

Figure 1A:
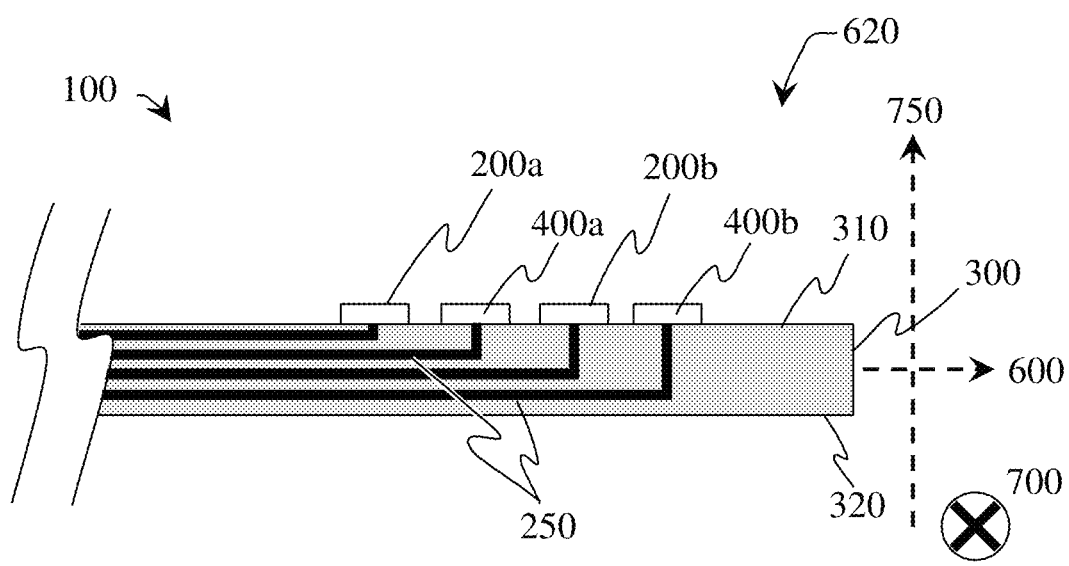
Figure 1B:
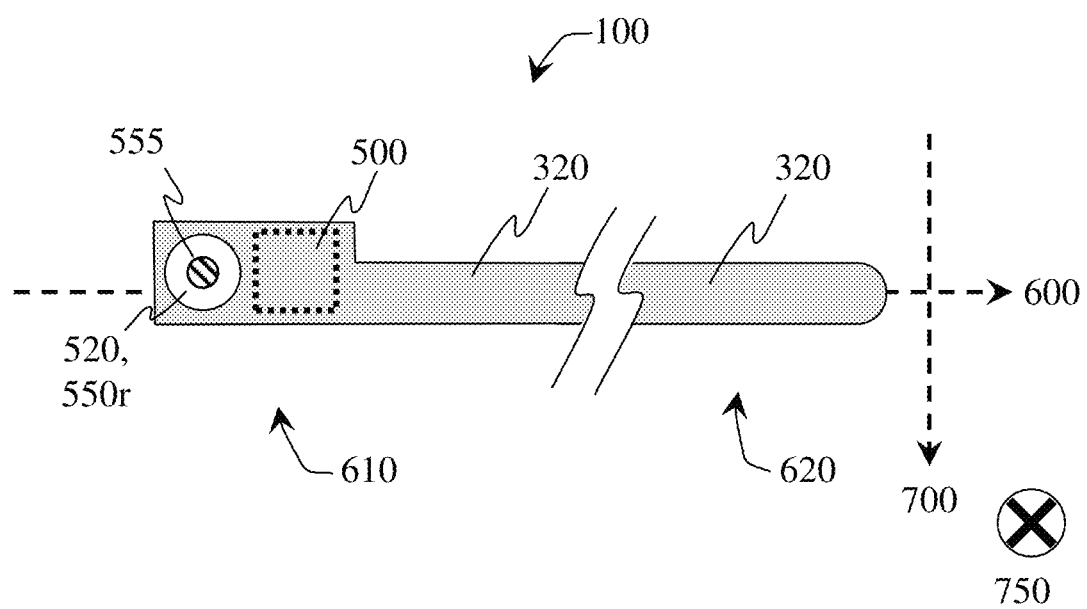
Figure 1C:
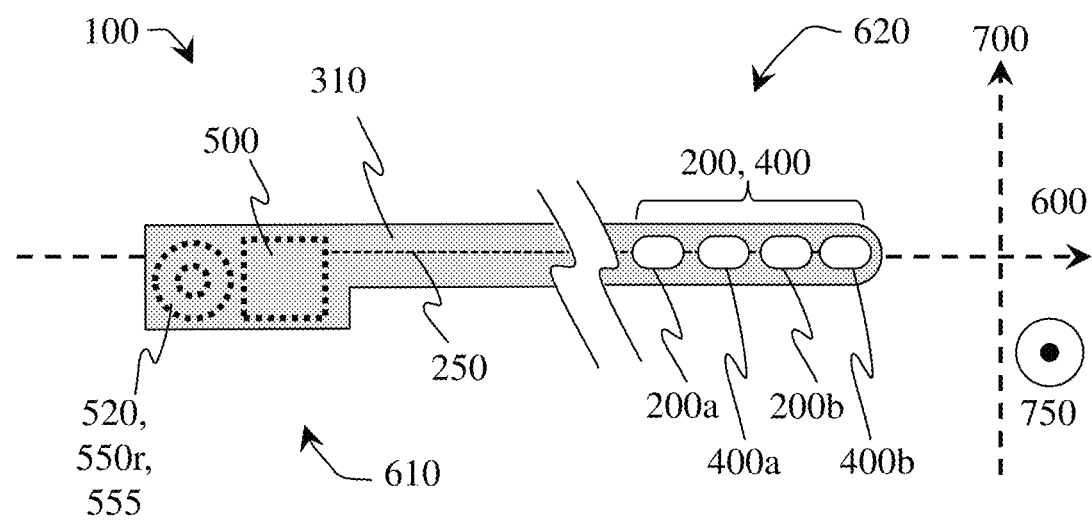
Figure 1D:
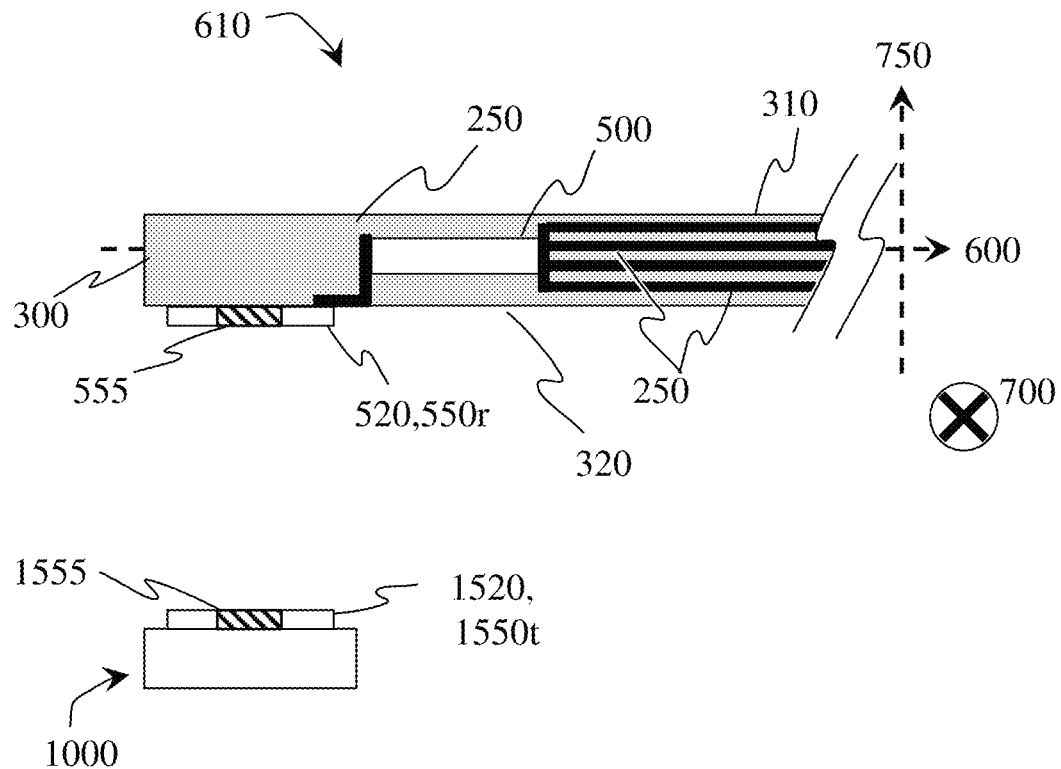
Figure 2:
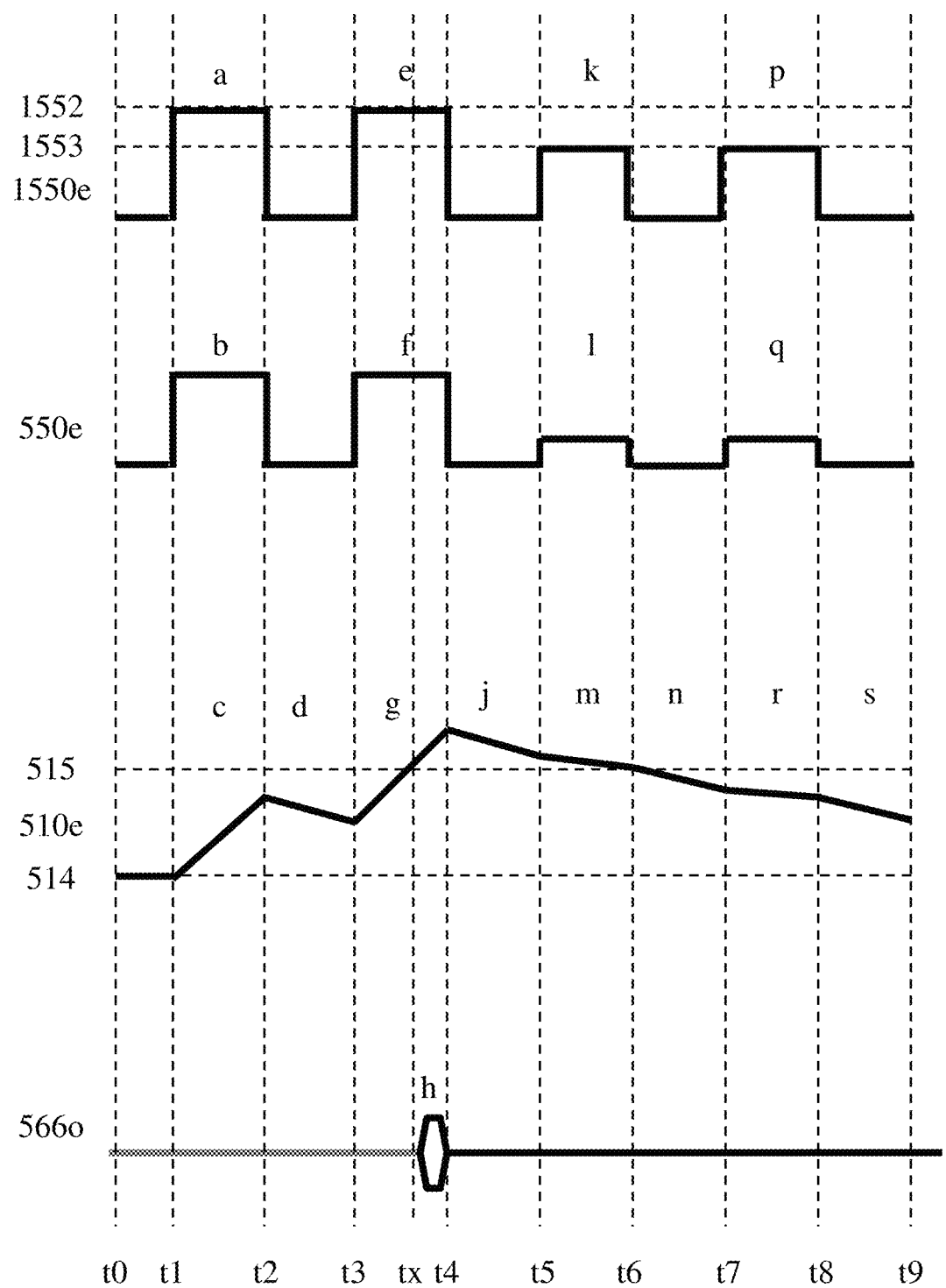
Figure 3A:
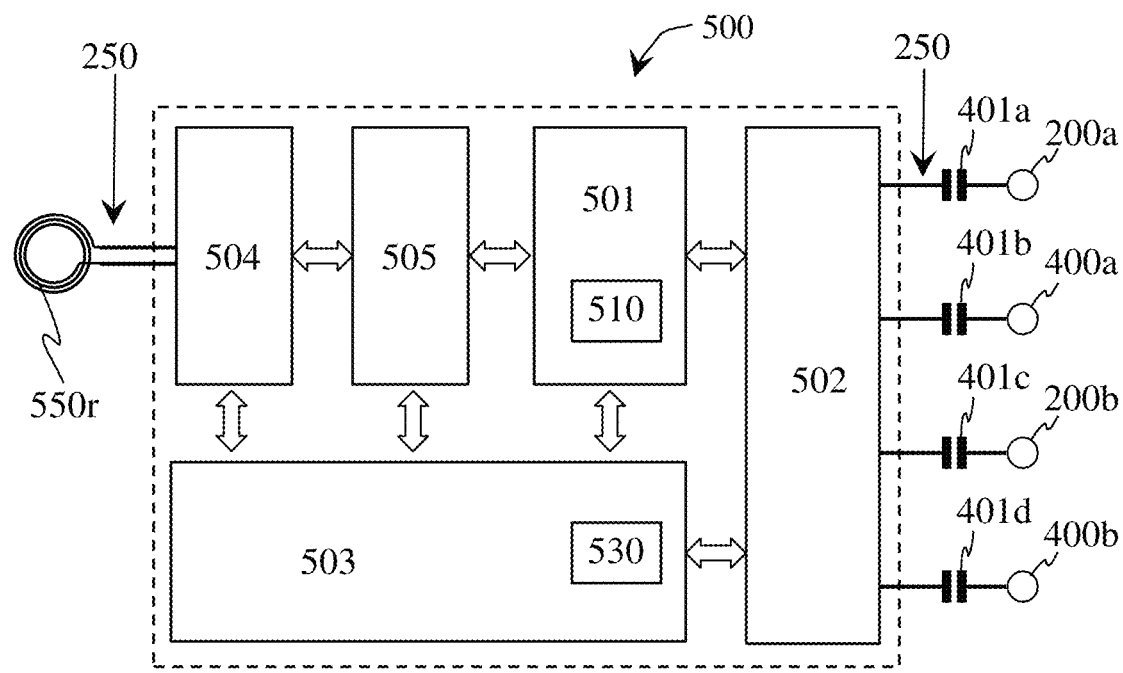
Figure 3B:
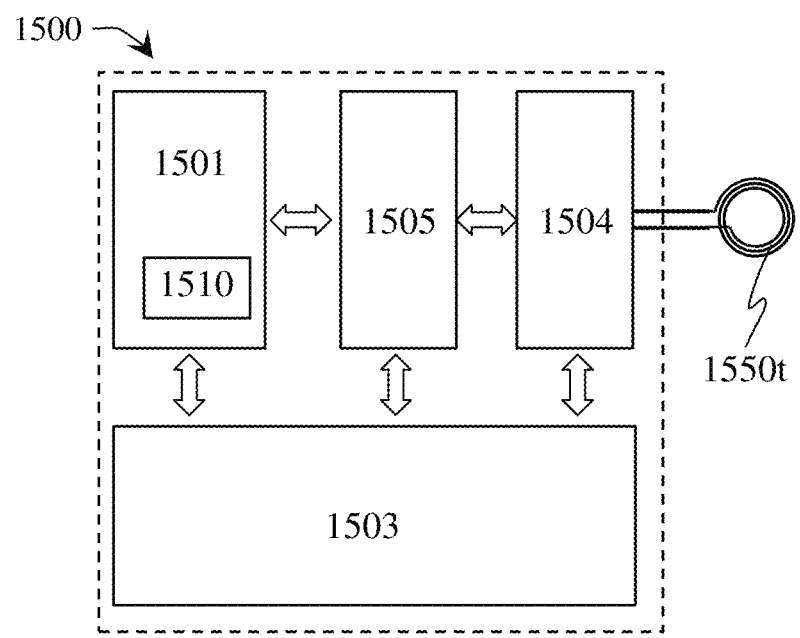
Figure 4:
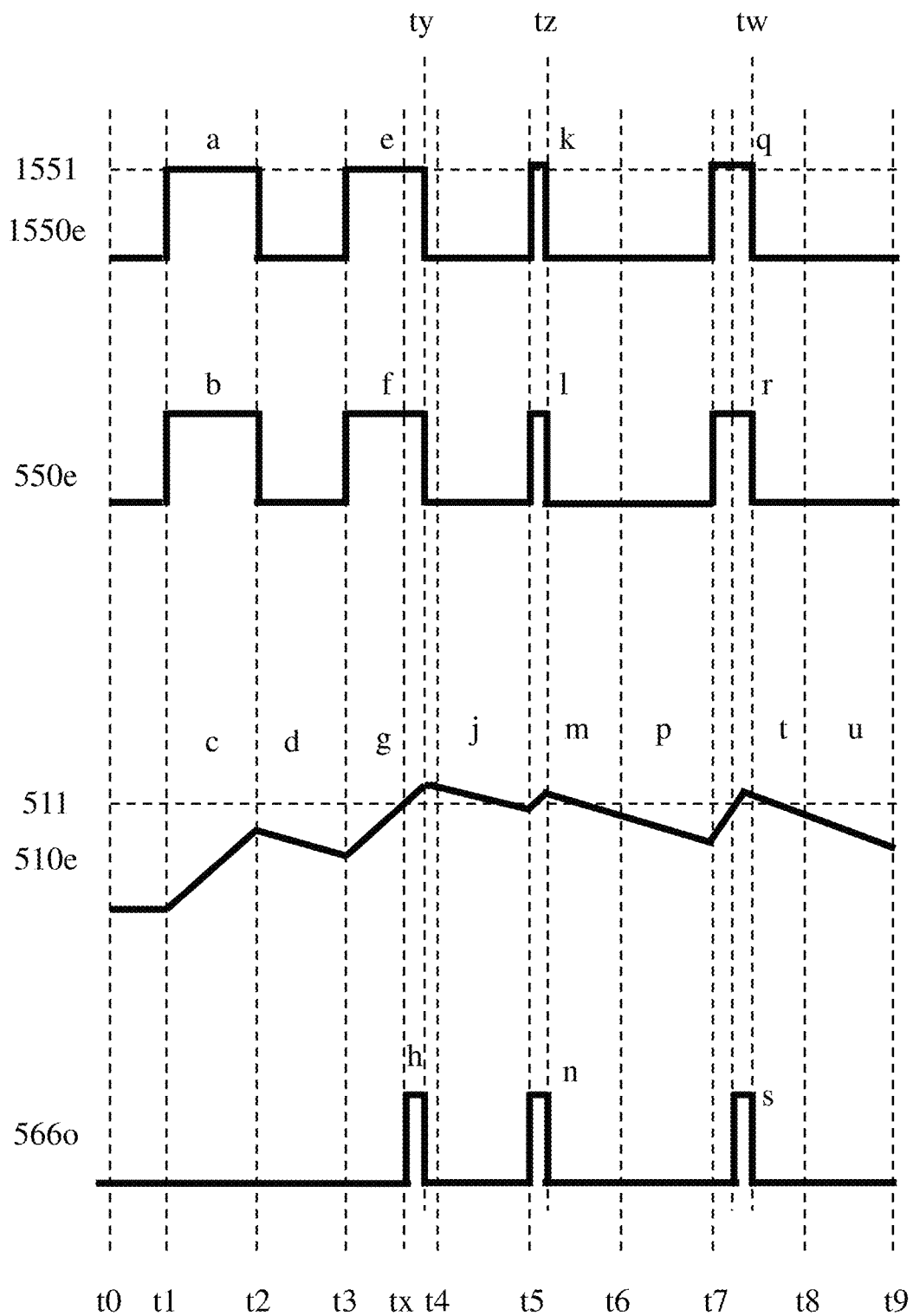
Figure 5:
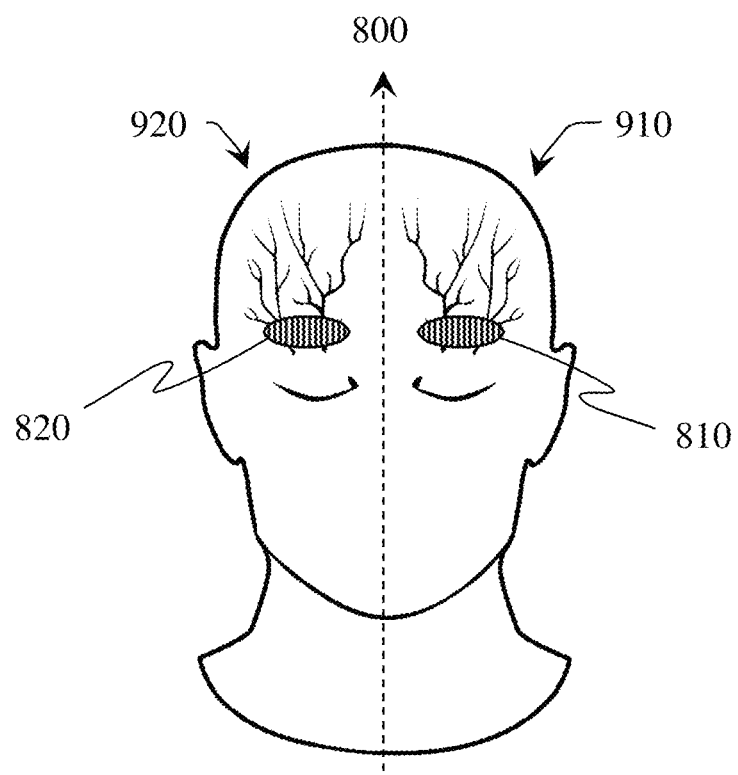
Figure 6:
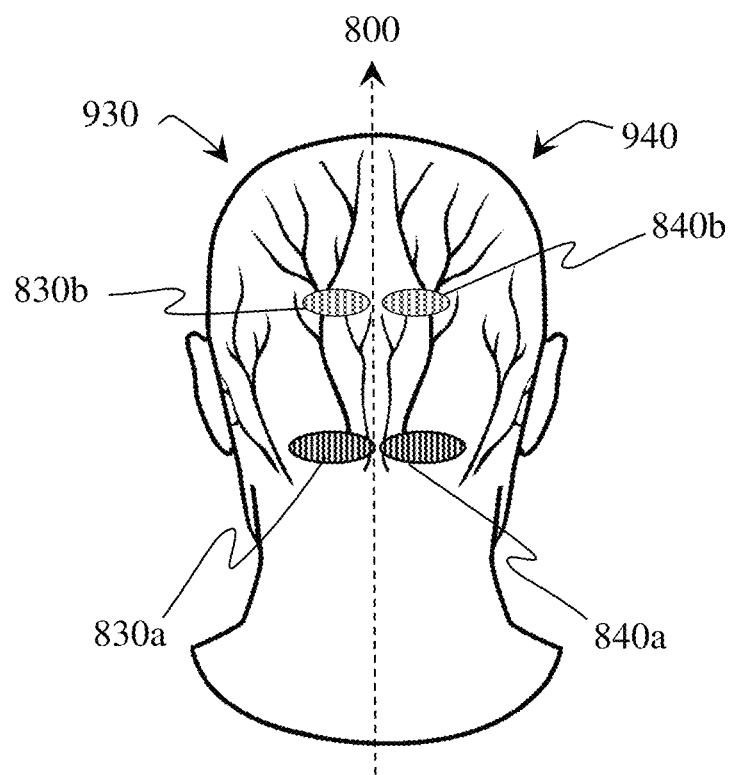
Figure 7:
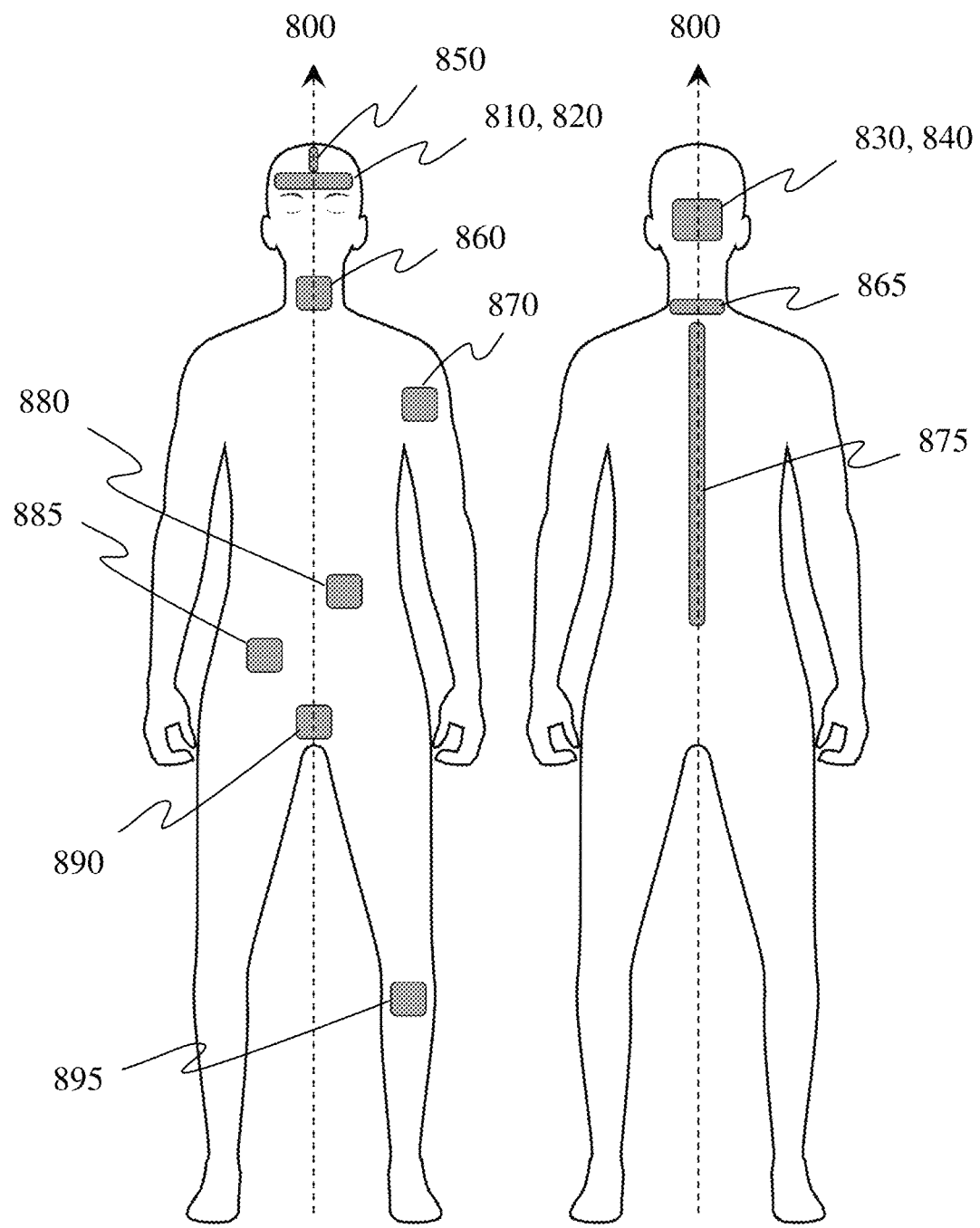
Figure 8:
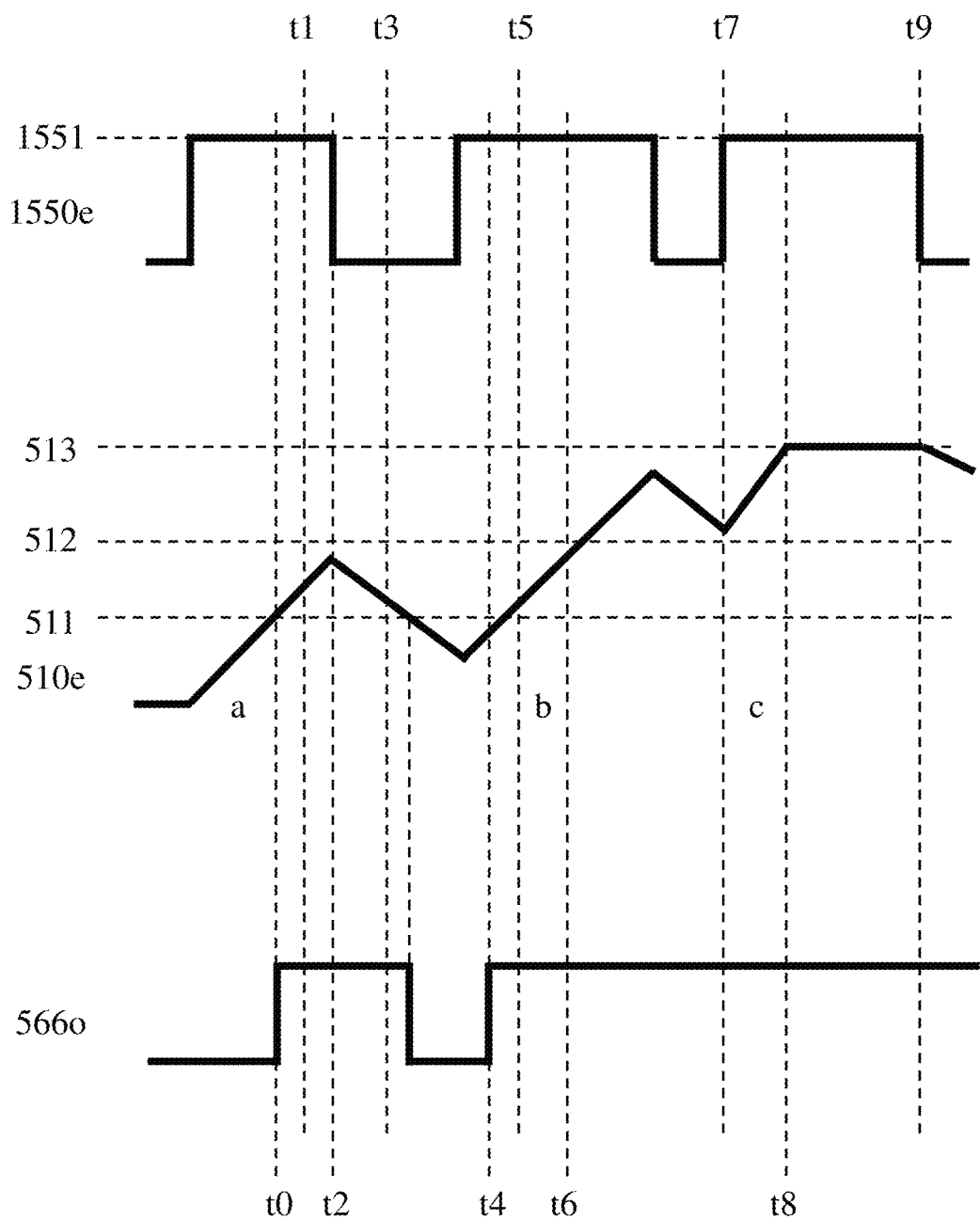
Figure 9A:
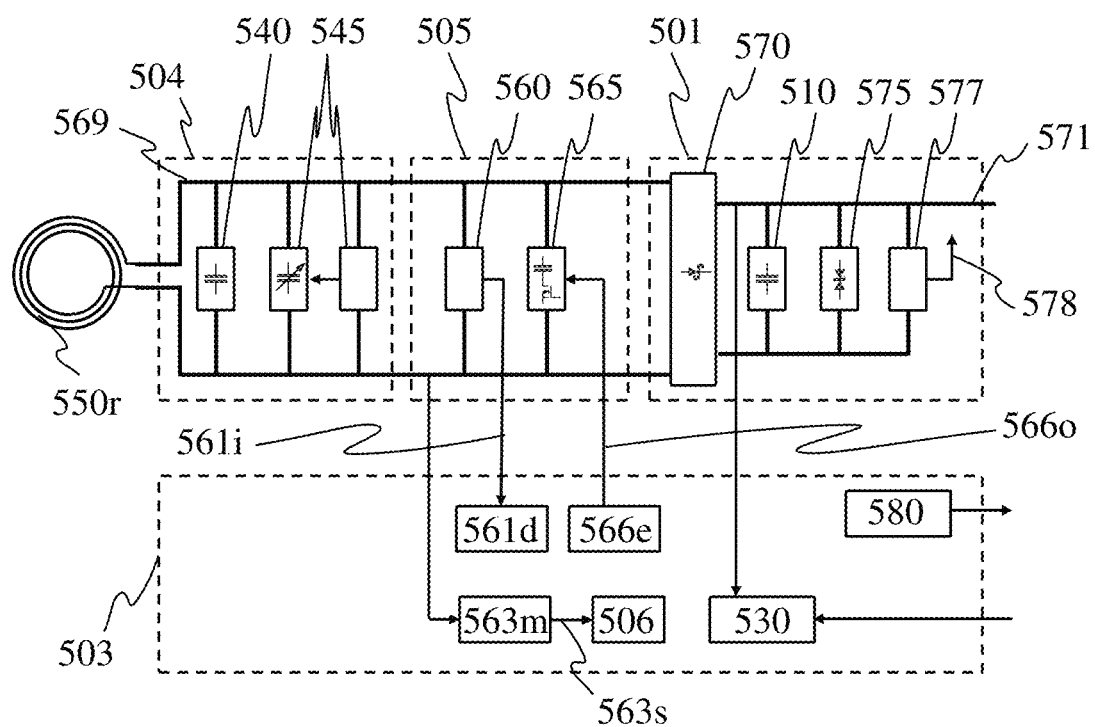
Figure 9B:
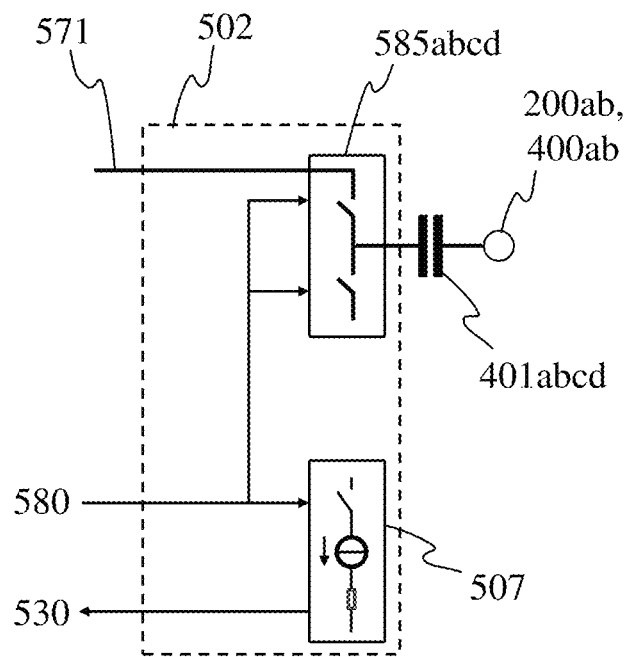
Figure 10:
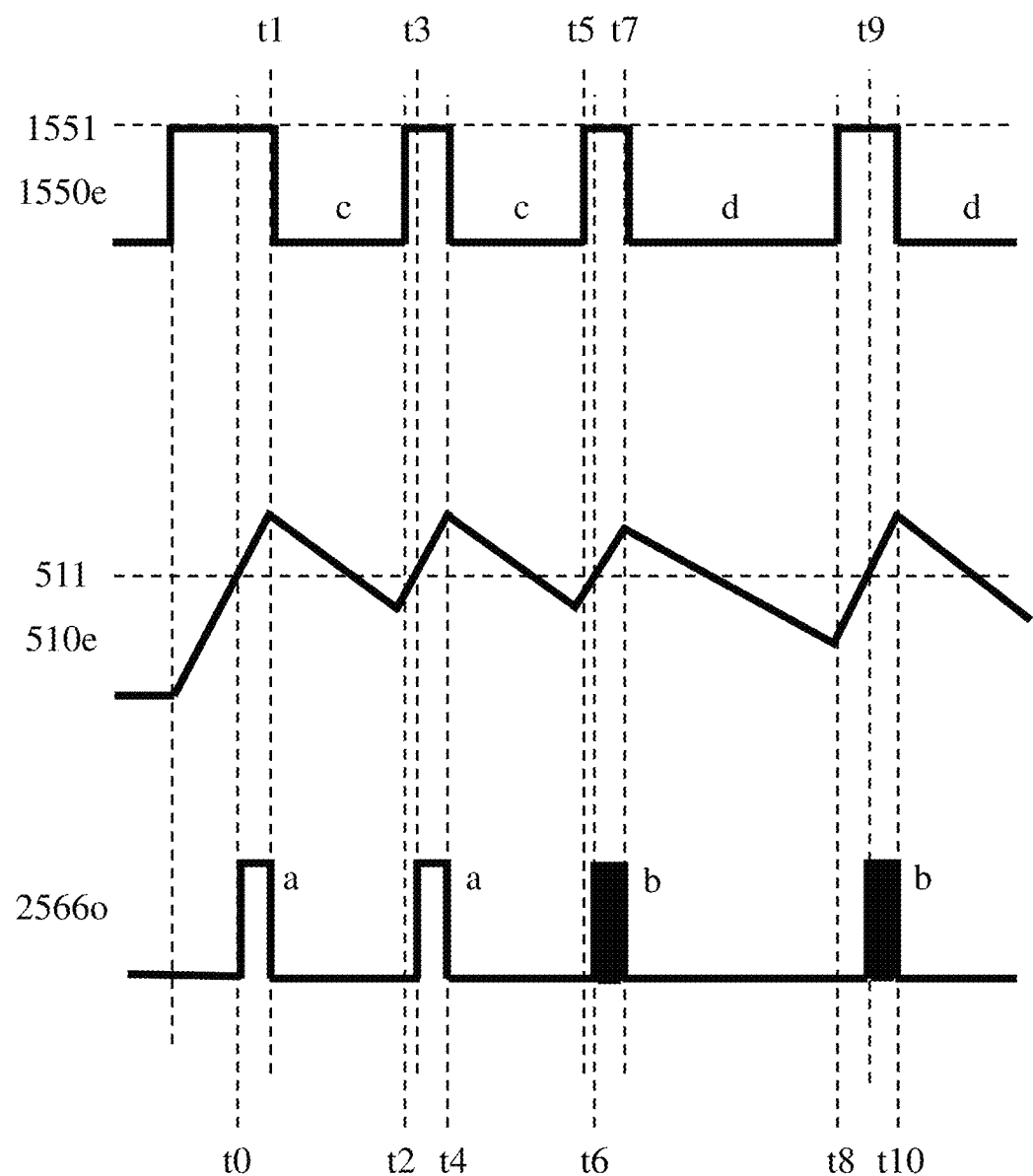

The skilled person will also realize that the signal and timing depictions in this disclosure are schematic and intended to highlight relevant aspects of the embodiments. For example, when the embodiments are implemented, moments depicted as simultaneous may be separated by a delay, signal flanks depicted as vertical may have a slope, waveforms depicted as square may be deformed and/or rounded, additional delays may be present:

FIG. 1A is a longitudinal (or side) cross-section through an implantable stimulator;

FIG. 1B is a top plan view of an implantable stimulator;

FIG. 1C is a bottom plan view of an implantable stimulator;

FIG. 1D is a further longitudinal or side cross-section through an implantable stimulator;

FIG. 2 schematically depicts data or signal communication and energy transmission signals generated when carrying out a method of controlling the wireless energy transfer;

FIG. 3A schematically depicts a suitable pulse generator or pulse energy controller;

FIG. 3B schematically depicts a suitable associated energy transmission device;

FIG. 4 schematically depicts data or signal communication and energy transmission signals generated when carrying out a further method of controlling the wireless energy transfer;

FIG. 5 and FIG. 6 depict examples of nerves that may be stimulated to treat headaches;

FIG. 7 depicts examples of nerves that may be stimulated for other treatments;

FIG. 8 schematically depicts the use of up to three protection levels;

FIGS. 9A and 9B depict two views of a more detailed schematic of a suitable pulse generator; and FIG. 10 schematically depicts still further methods of controlling the wireless energy transfer.

DETAILED DESCRIPTION

An implantable device, and methods for controlling an implantable device will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may affect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted.

The description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, "at least one of A, B, and C" indicates A or B or C or any combination thereof. As used herein, the singular form of a word includes the plural, and vice versa, unless the context clearly dictates otherwise. Thus, the references "a", "an", and "the" are generally inclusive of the plurals of the respective terms.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

As used herein, ranges are used herein in shorthand, so as to avoid having to list and describe each and every value within the range. Any appropriate value within the range can be selected, where appropriate, as the upper value, lower value, or the terminus of the range.

The words "comprise", "comprises", and "comprising" are to be interpreted inclusively rather than exclusively. Likewise the terms "include", "including" and "or" should all be construed to be inclusive, unless such a construction is clearly prohibited from the context. The terms "comprising" or "including" are intended to include embodiments encompassed by the terms "consisting essentially of" and "consisting of". Similarly, the term "consisting essentially of" is intended to include embodiments encompassed by the term "consisting of". Although having distinct meanings, the terms "comprising", "having", "containing" and "consisting of" may be replaced with one another throughout the description.

"About/approximately" means a referenced numeric indication plus or minus 10% of that referenced numeric indication. For example, the term "about 4" would include a range of 3.6 to 4.4. All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise.

"Typically" or "optionally" means that the subsequently described event or circumstance may or may not occur, and that the description includes instances where said event or circumstance occurs and instances where it does not.

Implantable devices or implants may be configured and arranged to provide many functions. For example:
 to measure one or more environmental parameters;
 to measure one or more biological parameters;
 to release one or more substances;
 to provide one or more electrical pulses to tissue;
 or any combination thereof.

The embodiments are described mainly using example of implantable stimulators as these typically require a more complex control of energy. However, the skilled person will realize that, as the disclosure is related to the control of energy, it may be implemented in any suitable implantable device that can wirelessly receive electrical energy. The device may be particularly advantageous when implemented in an implantable stimulator because these typically have a relatively high power usage.

FIGS. 1A and 1D depict longitudinal cross-sections, and FIGS. 1B & 1C depict plan views, of an implantable device 100, configured and arranged to provide energy to human or animal tissue as a treatment for cosmetic and/or therapeutic reasons. It may also be described as an implantable stimulator 100.

The stimulator 100 comprises an implantable first substrate portion 610 and an implantable second substrate portion 620. The first substrate portion 610 may also be described as a proximal end. The second substrate portion 620 may also be described as a distal end. FIG. 1A depicts the second substrate portion 620, FIG. 1D depicts the first substrate portion 610, FIGS. 1B and 1C depict both the first 610 and second 620 substrate positions.

The stimulator 100 further comprises:
 an electrode array 200, 400, comprised in the second substrate portion 620, with at least two electrodes 200, 400. Optionally, the second substrate portion 620 may be conformable.

In this example, one or more electrodes are provided of a first 200a, 200b type and one or more electrodes are provided of a second type 400a, 400b. The electrodes 200, 400 are comprised in the first 310 or second 320 surface, and each is configurable for transferring energy, in use, to (as a stimulation electrode) and/or from (as a return electrode) human or animal tissue. In this context, an array may be considered a systematic arrangement of two or more electrodes 200a, 200b, 400a, 400b. One-dimensional (1D), Two-dimensional (2D), or Three-dimensional (3D) arrays may be provided. Optionally, they may be arranged in rows and/or columns.

In this example, the second substrate portion 620 comprises a 1D array with two electrodes of the first type 200a, 200b and two electrodes of the second type 400a, 400b. However, as described below, any number and type of electrodes may be used.

The implantable stimulator 100 further comprises:
 one or more electrical and/or electronic components, comprised in the first substrate portion 610;
 an optional pulse generator 500 (depicted in FIG. 1B) for generating one or more therapeutic electrical stimulation pulses. It may also be called a pulse energy controller. In this example, the optional pulse generator 500 is comprised in the first substrate portion 610. The pulse energy controller 500 may, for example, comprise a suitably configured and programmed processor, controlling one or more parameters of the stimulation energy pulses, such as an intensity, a duration, a waveform shape, a frequency, and a repetition rate using one or more software or firmware methods. Additionally or alternatively, a hardware-based solution may be used, such as a state-machine implemented in an ASIC (Application-Specific Integrated Circuit). It may operate in a stand-alone mode, or it may be in regular communication with an external controller, or some combination thereof;

a substrate 300 extending longitudinally from the first substrate portion 610 to the second substrate portion 620 along a longitudinal axis 600; and one or more energy receivers 550r (not depicted in FIG. 1A) for wirelessly receiving energy from an associated energy transmission device 1000 (only depicted in FIG. 1D) when the associated energy transmission device 1000 is proximate. As described below, the energy receivers 550r are generally configured and arranged to wirelessly receive energy, and to transfer at least a portion of the energy to one or more electrical and/or electronic components comprised in the implantable device 100.

In this example, the one or more energy receivers 550r are comprised in the first substrate portion 610, and further configured to transfer at least a portion of the energy received to the at least two electrodes 200, 400. If the pulse generator 500 is included, the one or more energy receivers 550r are configured to transfer at least a portion of the energy to the pulse generator 500 and/or a portion to the at least two electrodes 200, 400.

Optionally, the second substrate portion 620 may be conformable. Additionally or alternatively, the first substrate portion 610 may be conformable.

Optionally, the substrate 300 may comprise one or more conformable foil-like substrate portions, as explained below. Additionally or alternatively, the substrate 300 may comprise two or more adjacent polymeric substrate layers.

The substrate 300 comprises a first 310 and second 320 surface, defining one or more thicknesses. Optionally, the surfaces 310, 320 may be substantially planar.

As depicted in FIGS. 1B and 1D, the one or more energy receivers 550r are comprised in the second surface 320. Additionally or alternatively, the energy receivers 550r may be comprised in the first surface 310 and/or comprised between the first 310 and second surface 320.

As depicted in FIG. 1D, the pulse energy controller 500 is comprised between the first 310 and second 320 surfaces. Alternatively, the pulse controller 500 may be comprised in the first 310 or 320 surface. Alternatively, the pulse controller 500 may be divided into more than one electrical and/or electronic components, allowing the pulse controller 500 to be comprised between two surfaces 310, 320 and comprised in one or more surfaces 310, 320.

The implantable stimulator 100 also comprises:

one or more electrical interconnections 250, between the first substrate portion 610 and the first 200a, 200b and the second 400a, 400b electrodes, for transferring electrical energy as one or more electrical treatment stimulation pulses to the first electrodes 200a, 200b and/or the second electrodes 400a, 400b. The one or more electrical interconnections 250 are comprised between the first surface 310 and the second 320 surfaces. In other words, a plurality of electrical interconnections 250 are comprised between the first 310 and second 320 surfaces.

If the separation between the first substrate portion 610 and the second substrate portion 620 is relatively large, a further substrate portion of the substrate may be provided which comprises no stimulation electrodes. The length of this further substrate portion with no stimulation electrodes may be configured and arranged to allow the first substrate portion 610 and the second substrate portion 620 to be located at different positions on and/or in the body.

In this disclosure, the conformability of the at least two electrodes 200, 400 is determined to a high degree by the one or more of the following:

the conformability of the substrate 300 proximate the electrodes 200, 400;

the arrangement and positions of the electrodes 200, 400;

the materials and dimensions (or extent) of the materials comprised in the electrodes 200, 400;

the arrangement and positions of the one or more interconnections 250 proximate the electrodes 200, 400; and the materials and dimensions (or extent) of the materials comprised in the interconnections 250.

By suitable configuration, arrangement and optimization, an implantable substrate portion with at least two electrodes 200, 400 may be provided which is further configured and arranged to be foil-like (or film-like) and highly conformable.

As depicted, the substrate 300 is preferably elongated along the longitudinal axis 600, having a tape-like shape, allowing the first substrate portion 610 to be disposed further away from the position of the electrodes 200, 400. This provides a high degree of flexibility if the proximal 610 end and distal end 620 of the stimulator 100 have different transverse cross-sections.

If the substrate 300 is arranged substantially planar (for example, by allowing the substrate 300 to conform to a planar surface), the first 310 and second 320 surfaces are disposed along substantially parallel transverse planes 600, 700. As depicted in FIG. 1A and FIG. 1C, the first surface 310 lies in a plane comprising the longitudinal axis 600 and a first transverse axis 700—the first transverse axis 700 is substantially perpendicular to the longitudinal axis 600. As depicted in FIGS. 1A and 1D, the plane of the first surface 310 is substantially perpendicular to the plane of the cross-section drawing (substantially perpendicular to the surface of the paper). As depicted in FIG. 1A and FIG. 1B, the second surface 320 lies in a plane comprising the longitudinal axis 600 and the first transverse axis 700. As depicted in FIGS. 1A and 1D, the plane of the first surface 310 is substantially perpendicular to the plane of the cross-section drawing (substantially perpendicular to the surface of the paper).

If the substrate 300 is conformable and foil-like, the substrate 300 typically has a maximum thickness of 0.5 millimeter or less, proximate the first 200a, 200b and second 400a, 400b electrodes.

A substrate thickness may be considered as a perpendicular distance between corresponding points on the first 310 and second surfaces 320. This is preferably determined when the substrate 300 conforms to a planar surface.

As depicted in FIG. 1A, the substrate 300 thickness is an extent along a second transverse axis 750—this second transverse axis 750 is substantially perpendicular to both the longitudinal axis 600 and the first transverse axis 700—it lies in the plane of the drawing (along the surface of the paper) as depicted. The first surface 310 is depicted as an upper surface and the second surface 320 is depicted as a lower surface. The extent along the second transverse axis 750 (thickness) may also be described as a dimension of a cross-section in the transverse plane 700, 750.

The thickness may therefore be determined by a perpendicular distance along the second transverse axis 750 between corresponding points on the first 310 and second surfaces 320. The maximum thickness of a conformable and/or foil-like substrate 300 along the second substrate portion 620 is preferably 0.5 mm or less, preferably 0.3 millimeters or less, even more preferably 0.2 millimeters or less, yet more preferably 0.1 millimeters or less. In general, the lower the maximum thickness (in other words, the thinner the substrate), the higher the degree of conformance Additionally or alternatively, the maximum thickness may be determined proximate the first 200a, 200b and second 400a, 400b electrodes.

To clarify the differences between the different views depicted, the axes are given nominal directions:
- the longitudinal axis 600 extends from the first substrate portion 610 (not depicted in FIG. 1A) on the left, to the first substrate portion 620 (not depicted in FIG. 1D), depicted on the right of the page;
- the first transverse axis 700 extends into the page as depicted in FIG. 1A and FIG. 1D; and
- the second transverse axis 750 extends from bottom to top as depicted in FIG. 1A and FIG. 1D.

The substrate 300 may be configured and arranged as a multilayer, comprising two or more adjacent polymeric substrate layers having the first 310 and second 320 surface. The one or more electrical interconnections 250 are also comprised between the first 310 and second 320 surfaces. However, it is not necessary that the two or more polymeric layers and/or interconnections have similar extents along the first transverse axis 700. In other words, within the context of this disclosure, there may be regions where an interconnection 250 is sandwiched between regions of polymeric substrate (appears as a multilayer in a longitudinal cross-section), adjacent to regions where the polymeric substrate is substantially contiguous. Similarly, there may be regions where an interconnection 250 is sandwiched between two polymeric substrate layers (appears as a multilayer in a longitudinal cross-section), adjacent to regions where the substrate comprises two adjacent substrate layers. Similarly, a substrate comprising two or more polymeric substrate layers may be modified (physically and/or chemically), such that it appears to be one layer of polymeric substrate.

These polymeric substrate layers are selected for suitability to be conformable, and to comprise the one or more electrical interconnections 250. Preferably, the polymeric substrate materials are also biocompatible and durable, such as a material selected from the group comprising silicone rubber, siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate. Suitable examples of polymers, including LCP (Liquid Crystal Polymer) films, are described in "Polymers for Neural Implants", Hassler, Boretius, Stieglitz, Journal of Polymer Science: Part B Polymer Physics, 2011, 49, 18-33 (DOI 10.1002/polb.22169), In particular, Table 1 is included here as reference, depicting the properties of Polyimide (UBE U-Varnish-S), Parylene C (PCS Parylene C), PDMS (NuSil MED-1000), SU-8 (MicroChem SU-8 2000 & 3000 Series), and LCP (Vectra MT1300).

Conformable foil-like substrates 300 are configured to follow the contours of the underlying anatomical features very closely by being flexible. Very thin foil-like substrates 300 have the additional advantage that they have increased flexibility. In general, thinner elements allow placement in a plurality of subcutaneous locations and provide a higher degree of comfort to the subject.

Most preferably, the polymeric substrate layers comprise an LCP, Parylene, and/or a Polyimide. LCPs are chemically and biologically stable thermoplastic polymers which allow for hermetic sensor modules having a small size and low moisture penetration. Advantageously, an LCP may be thermoformed allowing complex shapes to be provided. Very thin (and subsequently very conformable) and very flat (highly planar) layers of an LCP may be provided. For fine tuning of shapes, a suitable laser may also be used for cutting. For example, a conformable foil-like substrate 300 of LCP may have a thickness (extent along the second transverse axis 750) in the range 50 microns (um) to 720 microns (um), preferably 100 microns (um) to 300 microns (um). For example, values of 150 um (micron), 100 um, 50 um, or 25 um may be provided. The extent along the second transverse axis 750 (thickness) may also be described as a dimension of a cross-section in the transverse plane 700, 750.

When conforming to a substantially planar surface, the foil-like surface 300 is substantially comprised in a plane with a transverse extent substantially perpendicular to the longitudinal axis 600, wherein the planar width may be determined by a perpendicular distance between corresponding points on outer surfaces edges of the planar foil-like substrate 300 along the respective transverse extent. As depicted, this is along the first transverse axis 700. For example, electrode 200, 400 widths of 2 mm to 20 mm may be provided using LCP. The extent along the first transverse axis 700 (width) may also be described as a dimension of a cross-section in the transverse plane 700, 750. Typically, such a conformal foil-like substrate has an average transverse extent along the second transverse axis 750 (thickness) which is equal to or less than the average transverse extent along the first transverse axis 700 (planar width).

At room temperature, thin LCP films have mechanical properties similar to steel. This is important as implantable substrates 300 should be strong enough to be implanted, strong enough to be removed (explanted), and strong enough to follow any movement of the neighboring anatomical features and/or structures without deteriorating.

LCP belongs to the polymer materials with the lowest permeability for gases and water. LCP's can be bonded to themselves, allowing multilayer constructions with a homogenous structure. In contrast to LCPs, polyimides are thermoset polymers, which require adhesives for the construction of multilayer substrate portions with at least two electrodes. Polyimides are thermoset polymer material with high temperature and flexural endurance.

An LCP may be used, for example, to provide conformable substrate 300 as a multilayer—in other words, two or more adjacent polymeric substrate layers. For example, these may be layers of 25 um (micron) thickness.

For example, one or more electrical interconnections 250 may be provided between the first 310 and second 320 surfaces by metallization. These may be conductors embedded in the substrate 300—for example, by having a single polymer layer and applying conductive material using suitable deposition techniques known from the semiconductor industry. For example, the substrate may comprise a first conformable layer and at least one second conformable layer, wherein a plurality of electrical interconnection layers 250 are positioned along the first layer using a deposition technique, and wherein the at least one second layer is secured to the first layer to cover the plurality of electrical interconnections.

If two or more adjacent polymeric substrate layers are provided, an interconnection layer may be provided using suitable techniques, for example, those from the semiconductor industry. The polymeric substrate layers may also be considered adjacent when one of more adhesion layers are used between them.

Lamination may also be used to provide a substrate 300 with the desired physical and chemical properties, and/or to provide a convenient method of manufacture. For example, a substrate 300 may comprise three laminated polymer layers: two high temperature thermoplastic layers with a low-temperature layer (bond-ply) in between, and high-temperature layers towards the first surface 310 and second surface 320.

In another example, two layers of silicone may be provided as polymeric substrate layers: one layer of silicone is provided, metal is patterned on one of its outer surfaces, and a second layer of silicone is added over the metal patterning by, for example, jetting, over-moulding, or spin-coating.

The electrical interconnections 250 may comprise one or more conductors, such as a metal, formed as required—for example, in one or more conductive elements: wire, strand, foil, lamina, plate, and/or sheet. They may be a substantially contiguous (one conductor). They may also comprise more than one conductor, configured and arranged to be, in use, electrically connected with each other—in other words, the one or more conductors are configured and arranged to be substantially electrically contiguous in use.

Alternatively, the one or more electrical interconnections 250 may be comprised in one or more conductive interconnection layers 250, the one or more conductive interconnection layers being comprised between two adjacent polymeric substrate layers. As depicted in FIG. 1A and FIG. 1D, a plurality of interconnections may be provided at different dispositions (or depths) between the first surface 310 and the second surface 320.

An interconnection 250 in the context of this disclosure is not configured or arranged to be, in use, in contact with human or animal tissue. For example, this may be done by embedding the one or more interconnections 250 in one or more layers of a low conductance or insulating polymer, such as LCP. Additionally or alternatively, one or more encapsulation layers may be used.

One or more interconnection layers 250 may also be provided by metallization using techniques from the PCB (Printed Circuit Board) industry, such as metallization with a bio-compatible metal such as gold or platinum. Electroplating may be used. Layers comprising LCP films are particularly suitable for metallization. These electrical interconnections 250 and/or interconnect layers 250 are configured to transfer electrical energy as one or more electrical treatment stimulation pulses from the pulse generator 500 to the first electrodes 200a, 200b and/or the second electrodes 400a, 400b.

Using suitable polymeric substrate materials, such as an LCP film, allows the conformable foil-like (or film-like) substrate 300 and the at least two electrodes 200, 400 to have a high width-to-height ratio, providing a bio-compatible electronic foil (or film), or bio-electronic foil (or film). For example, when the substrate 300 is arranged to conform to a substantially planar surface, the ratio of maximum planar width 700 to maximum thickness 750 proximate the first 200a, 200b and second 400a, 400b electrodes may be 7:1 or higher, preferably 10:1 or higher, more preferably 15:1 or higher, yet more preferably 30:1 or higher, even more preferably 50:1 or higher. Ratios of 100:1 or higher may also be advantageous, and may be provided using one or more mechanically strong substrate layers of an LCP film, with a width of approximately 20 mm and a thickness of approximately 0.2 mm. This provides a high degree of flexibility, and therefore also a high degree of conformability. Additional measures may also be taken to increase the degree of conformability in the first transverse direction 700, such as varying the width of the substrate, adding one or more undulations and/or providing bending points.

When using a single row of electrodes 200, 400 and/or electrodes 200, 400 with a smaller width, the width may be, for example, four mm with a thickness of approximately 0.2 mm—this is a ratio of approximately 20:1. Proximate the pulse generator 500, greater extents may be required which further depend, to a high degree, on the dimensions of the electronic components used, for example, a width of twenty mm and a thickness of three mm. This is a ratio of approximately 6.67:1.

As depicted in the example of FIG. 1A, the second substrate portion 620 of the substrate 300 comprises:
two electrodes 200a, 200b of a first type, comprised in the first surface 310, and
two electrodes 400a, 400b of a second type, also comprised in the first surface 310. From proximal end 610 to the distal end 620, the order depicted is 200a, 400a, 200b, 400b—in other words, each electrode of the first type 200a, 200b is proximate an electrode of the second type 400a, 400b and comprised in the same surface 310.

The substrate 300 comprises an electrical interconnection 250 between each electrode 200a, 400a, 200b, 400b and the pulse generator 500. In this embodiment, each electrical interconnection 250 is configured and arranged such that each electrode 200a, 400a, 200b, 400b is electrically connected substantially independently—consequently, one of the operating modes available by suitably configuring the pulse generator 500 is substantially independent operation. The pulse generator 500 may be configured using one or more hardware, firmware and/or software parameters.

Although depicted schematically in FIG. 1A (and FIG. 1D) as individual connections 250 at different distances between the first 310 and second 320 surfaces, the skilled person will also realize that the same interconnections may be provided by a suitably configured interconnections 250 (or an interconnection layer 250) at approximately the same distance between the first 310 and second 320 surfaces.

"Comprised in" the first 310 or second 320 surface means that the electrodes 200a, 400a, 200b, 400b are attached to (or at least partially embedded in) the surface. Preferably, they are relatively thin (for example, if the substrate is arranged to conform to a substantially planar surface, it may have an extent along the second transverse axis 750 of 20 to 50 microns or less. Thinner electrodes may also be used to further increase the degree of conformability, for example 1 micron or less), and be attached to (or at least partially embedded in) the surface.

The electrodes 200, 400 may comprise a conductive material such as gold, platinum, platinum black, TiN, IrO2, iridium, and/or platinum/iridium alloys and/or oxides. Conductive polymers, such as Pedot, may also be used. Preferably, bio-compatible conductive materials are used. PCB/metallization techniques may be used to manufacture them on or in the first 310 and/or second 330 surfaces of the one or more polymeric substrate layers. Thicker metal layers are generally preferred over thinner metal layers for electrodes 200a, 200b, 400a, 400b because they can be subjected to bodily substances that may dissolve the metal. However, thicker metal layers typically increase rigidity (reduce conformability) proximate the thicker layer.

As depicted in FIG. 1, there is no substantial hardware difference between the first type 200a, 200b and second type 400a, 400b electrodes—any difference in functionality is determined in this example mainly by the configuration (one or more hardware, firmware and/or software parameters) of:
  the pulse generator 500;
  one or more energy receivers 550r;
  one or more electrical components comprised in the implantable device;
  the arrangement and routing of the interconnections 250;
  or any combination thereof.

One or more electrodes of the same type 200a, 200b or 400a, 400b may be operated substantially the same by suitable configuration of the implantable device 100—in other words, the stimulation energy applied to the electrodes 200, 400 is substantially the same at substantially the same time instance (usually measured as a voltage, a current, a power, an energy, a charge, or any combination thereof). This may also be used to anticipate and/or correct for a misalignment and/or lead migration—this is advantageous as it allows the configuration to be performed at least partially using software.

Additionally or alternatively, two or more electrodes 200, 400 may be configured and arranged, using one or more parameters of the implantable device 100, as a stimulation electrode or a return electrode. This may provide a higher degree of configurability as it only becomes necessary to implant the substrate 300 such that at least two of the electrodes are proximate the desired stimulation location.

In this embodiment 100, the electrodes of the first type 200a, 200b are nominally configured and arranged to be operated as a stimulation electrode.

The electrodes of the second type 400a, 400b are nominally configured to be operated as a return electrode—each is configured to provide, in use, an electrical return for one or more stimulation electrodes 200a, 200b. In other words, the electrical return 400a, 400b closes the electrical circuit. It may also be similarly configured to provide an electrical ground for a corresponding electrical energy source.

Three configurations are thus provided based on this nominal configuration: either:
  a stimulation/return electrode pair 200a/400a proximate the first surface 310 at that stimulation/return location; or
  a stimulation/return electrode pair 200b/400b proximate the first surface 310 at that stimulation/return location; or
  a combination thereof.

In general, one or more stimulation electrodes 200a, 200b may be provided in such a stimulator 100. The number, dimensions and/or spacings of the stimulating electrodes 200a, 200b may be selected and optimized depending on the treatment—for example, if more than one stimulation electrode 200a, 200b is provided, each stimulation electrode 200a, 200b may provide a different stimulation effect, a similar stimulation effect or the same stimulation effect.

To avoid a misalignment, a selection may be made of one or two electrodes 200a, 200b proximate the tissues where the effect is to be created. Two or more stimulation electrodes 200a, 200b may be made active at substantially the same time if stimulation over a larger area is required and/or at a location between the active stimulation electrodes 200a, 200b.

A stimulation electrode 200a, 200b may have, for example, dimensions in the order of six to eight mm along the longitudinal axis 600, and three to five mm along the first transverse axis 700, so approximately 18 to 40 square mm (mm2).

A substrate 300, suitable for an implantable stimulator, may comprise, for example, up to twelve stimulation 200a, 200b and return 400a, 400b electrodes over a length of 15 cm to allow for a correction for misalignment, or to simply allow the specialist to select the most effective stimulation location.

FIG. 1B depicts a view of the second surface 320 of the implantable first substrate portion 610 of the substrate 300 depicted in FIG. 1A. In other words, the second surface 320 is depicted in the plane of the paper, lying along the longitudinal axis 600 (depicted from bottom to top) and in the first transverse axis 700 (depicted from left to right). The second transverse axis 750 extends into the page. The first surface 310 is not depicted in FIG. 1B, but lies at a higher position along the second transverse axis 750 (into the page), and is also substantially parallel to the plane of the drawing. The substrate 300 is arranged to conform to a substantially planar surface.

In general:
  the second substrate portion 620 comprises substantially only one or more electrodes 200, 400 and one or more interconnections 250; and
  the first substrate portion 610 comprises one or more electrical components, disposed between the second 320 surface and the first 310 surface. Alternatively, the one or more electrical components may be at least partially disposed on the first surface 310 or on the second surface 320. Alternatively, the one or more components may be at least partially embedded in the first surface 310 or in the second surface 320.

Depending on, for example, the degree of embedding and the one or more electrical components used, the maximum thickness and/or planar width may be optimized. Components may be thinned to minimize the thickness. Components may include one or more energy receivers 550r and/or one or more pulse generators 500 to provide, in use, stimulation pulses to the electrodes 200, 400. Additional optional electrical components, such as an antenna (for example, a coil or dipole or fractal antenna), may also influence the thickness and/or width depending on the degree that they are embedded in the substrate.

Advantageously, the first substrate portion 610 comprises a pulse generator 500. Optionally, it may be disposed between the second 320 surface and the first 310 surface, as depicted In FIG. 1D. In FIGS. 1B and 1C, the position of the pulse generator 500 is depicted with dotted lines as it is not directly visible. Alternatively, the pulse generator 500 may be at least partially disposed on the first surface 310 or on the second surface 320. Alternatively, the pulse generator 500 may be at least partially embedded in the first surface 310 or in the second surface 320.

Depending on, for example, the degree of embedding and the one or more electrical components used for the pulse generator 500, the maximum thickness (maximum transverse extent along the second transverse axis 750) may be optimized. Additionally or alternatively, the maximum planar width (maximum transverse extent along the first transverse axis 700) may be optimized.

If the substrate 300 is configured and arranged to be conformable and/or foil-like, the maximum thickness (extent along the second transverse axis 750) of the implantable stimulator 100 proximate the pulse generator 500 may be five millimeters or less, preferably four millimeters or less, even more preferably three millimeters or less, the thickness being determined by a perpendicular distance between corresponding points on outer planar surfaces when the implantable stimulator 100 conforms to a substantially planar surface.

The stimulator 100 and the substrate 300 extend along the first transverse axis 700 (considered the planar width of the stimulator 100/substrate 300 when conforming to a substantially planar surface). The planar widths proximate the energy receivers and/or pulse generator 500 depend on, for example, the hardware and components used—typically, it is at least the width of the largest integrated circuit used. Additional optional electrical components, such as an antenna (for example, a coil or dipole or fractal antenna), may also influence the maximum planar width. The planar widths proximate the electrodes 200a, 200b, 400a, 400b depend on, for example, the conductors used for the electrodes 200a, 200b, 400a, 400b and the one or more interconnections 250—typically, it is at least the width of the first electrodes 200a, 200b or the second electrodes 400a, 400b.

FIG. 1C depicts a view of the first surface 310 of the implantable second substrate portion 620 of the substrate 300 depicted in FIGS. 1A and 1B. In other words, the first surface 310 is depicted in the plane of the paper, lying along the longitudinal axis 600 (depicted from bottom to top) and in the first transverse axis 700 (depicted from right to left). The second transverse axis 750 extends out of the page. This is the view facing the animal or human tissue which is stimulated (in use). The second surface 320 is not depicted in FIG. 1C, but lies at a lower position along the second transverse axis 750 (into the page), and is also substantially parallel to the plane of the drawing. The substrate 300 is arranged to conform to a substantially planar surface.

The one or more interconnections 250 are disposed between the first 310 surface and the second 320 surface, as depicted in FIGS. 1A and 1D. In FIG. 1C, they are depicted as a dotted line, representing the interconnections 250 (or suitably configured one or more interconnection layers 250) that have been provided for each of the electrodes 200a, 200b, 400a, 400b in this embodiment. A single dotted line 250 is depicted between the pulse generator 500 and the electrodes 200, 400 to indicate, in this example 100, that the interconnections 250 are at approximately the same disposition along the first transverse axis 700.

As depicted in FIG. 1C, the electrodes 200a, 200b, 400a, 400b each have a longitudinal extent (length) along the longitudinal axis 600 and a transverse extent (width) along the first transverse axis 700. Although depicted as similar, in practice, each electrode 200a, 200b, 400a, 400b may vary in shape, transverse cross-section, orientation and/or size (or extent), depending on the intended use and/or the desired degree of configurability.

After implantation of the stimulator 100, or at least of the conformable second substrate portion 620, comprising the at least two electrodes 200, 400, the electrical components may be configured and arranged to provide, in use, electrical energy to the one or more electrodes of the first type 200a, 200b with respect to the electrical return applied to the one or more electrode of the second type 400a, 400b.

If a configurable pulse generator 500 is included, the configurability of the stimulator 100 allows, before, during and/or after implantation of at least the second substrate portion 620 comprising the at least two electrodes 200, 400, the operation of the one or more electrodes 200a, 200b, 400a, 400b to be determined and/or adapted. The operation may also be reconfigured one or more times during the period that the stimulator 100 is implanted to optimize and/or prolong treatment. For example, the pulse generator 500 may be initially configured to nominally operate 200a and 400a as respectively a stimulation/return electrode pair. After implantation of at least the second substrate portion 620, insufficient stimulation may be observed and/or measured. If it is assumed to be due to a mainly longitudinal misalignment, the pulse generator 500 may be alternatively configured, using one or more parameters, to nominally operate 200b and 400b as respectively a stimulation/return electrode pair.

The stimulator 100 may be further configured and arranged to switch the pulse generator 500 under predetermined and/or controlled conditions between these configurations. It may be convenient to further consider these configurations as first and second electrode modes, and allow a user to select a mode as a preference and/or switch modes. Additionally or alternatively, the pulse generator 500 may switch modes under predetermined and/or controlled conditions.

Additionally or alternatively, other modes may also be provided—for example, configuring the pulse generator 500 to operate in:
- a first electrode mode, wherein electrical stimulation energy is provided to one or more electrodes of the first type 200a, 200b as one or more electrical treatment stimulation pulses, the one or more electrodes of the second type 400a, 400b being configured to provide, in use, a corresponding electrical return for the one or more first electrodes 200a, 200b; or
- a second electrode mode, wherein to one or more electrodes of the second type 400a, 400b as one or more electrical treatment stimulation pulses, the one or more electrodes of the first type 200a, 200b being configured to provide, in use, a corresponding electrical return for the one or more second electrodes 400a, 400b.

Again, the stimulator 100 may be further configured and arranged to switch the pulse generator 500 under predetermined and/or controlled conditions between these configurations or modes. Additionally or alternatively, a user may be allowed to select a mode as a preference and/or switch modes.

The skilled person will realize that the electrodes 200a, 200b, 400a, 400b may be configured to operate in more complex configurations, such as:
- 400a and 200a may be operated as respectively a stimulation/return electrode pair (reversing the original intended operation);
- 400b and 200b may be operated as respectively a stimulation/return electrode pair;
- if an intermediate stimulation is preferred, two or more electrodes 200a, 200b, 400a, 400b may be operated substantially simultaneously as one or more stimulation electrodes;
- one or more electrodes 200a, 200b, 400a, 400b may be operated as one or more return electrodes;
- electrode 400a operated as a stimulation electrode, in combination with electrode 200a and electrode 200b as return electrodes;
- electrode 400a and 200b operated as a stimulation electrode, in combination with electrode 200a and electrode 400b as a return electrode.

Alternatively or additionally, the shape, orientation, transverse cross-section, and/or size (or length) of one or more stimulation electrodes may be differently configured compared to one or more return electrodes.

A number of parameters and properties may be considered when configuring and arranging the substrate 300 proximate the at least two electrodes 200, 400 for conformability, such as:
- the transverse 700 and/or longitudinal extent 600 of the one or more electrodes 200a, 200b, 400a, 400b
- the thickness of the substrate 300, or the perpendicular distance between the first surface 310 and the second surface 320
- the materials comprised in the substrate 300, and their physical properties
- the number and extent of interconnections 250 and/or interconnection layers 250 between the first surface 310 and second surface 320.

There have been attempts to make traditional leads, such as cylindrical leads, much thinner to allow subcutaneous implantation and/or to increase comfort by flattening. But the surface area of the flattened electrodes may become disadvantageously small.

For example, a conventional 0.2 mm round lead with 1 cm long electrodes is estimated to result in an electrode with approximately 6 mm$^2$ electrode surface.

However, using the conformable second substrate portion 620 with at least two electrodes described herein, a relatively thin substrate 300 with dimensions of 0.2 mm thick, and four mm wide may be configured and arranged to provide approximately 35 mm$^2$ electrode surface in the same length. It is estimated that this may reduce impedance by a factor of approximately 35/6, and reduce energy consumption by approximately 35/6.

FIG. 1D depicts more details of the one or more energy receivers 550r—in this example, they are comprised in the second surface 320.

The implantable device 100 is further configured and arranged to transmit signals to the energy transmission device 1000. For example, signals carrying one or more parameters and/or one or more values, may be transmitted to give feedback to the energy transmission device 1000 about the status of the implantable device 100.

In this example, the one or more energy receivers 550r may be further configured and arranged to receive pulse energy and/or transmit signals. Energy and data may therefore be transmitted via the same channel. The data may be transmitted substantially simultaneously as energy pulses are received, or substantially not simultaneously or overlapping in time.

The associated energy transmission device 1000, also depicted in FIG. 1D, comprises:
- one or more energy transmitters 1550t, configured and arranged to wirelessly transmit energy. The one or more energy transmitters 1550t comprise one or more conductors, such as coils with one or more windings. They are configured to wirelessly transmit pulsed energy to the one or more energy receivers 550r when the energy transmission device 1000 is proximate to the implantable device 100. Preferably, the one or more energy transmitters 1550t are configured and arranged to cooperate with the one or more energy receivers 550r to provide a high degree of efficiency during wireless energy transfer.

For example, coils may be configured and arranged to convert the energy pulses to electromagnetic pulses for transmission. In general, electromagnetic signals, such as RF (radio-frequency) or microwaves, are advantageous as they typically are less sensitive to bandwidth and/or data rate issues. However, there may be some restrictions, such as the available frequency bands. In the implantable device, the coils comprised in the implantable device 100 are configured and arranged to convert magnetic energy to electrical energy.

Preferably, a permitted operating frequency, such as an ISM band, is used (in-band communication). The ISM radio bands are reserved internationally for industrial, scientific and medical (ISM) purposes other than telecommunications.

ISM frequencies include center frequencies 6.78 MHz, 13.56 MHz, 27.12 MHz, and 40.68 MHz providing bandwidths of 30 kHz, 14 kHz, 326 kHz, and 40 kHz, respectively.

The associated energy transmission device 1000 further comprises:
- an energy transmission controller 1500, configured and arranged to control one or more parameters of the one or more energy transmitters 1550t; and
- optionally, one or more mechanical attachment, such as a stud, hook or a magnet 1555, configured and arranged to co-operate with the implantable device 100 to reduce the risk of misalignment of the one or more energy transmitters 1550t and the one or more energy receivers 550r. For example, the implantable device 100 may also comprise a magnet 555 at a suitable location on the implantable device 100 to allow a docking due to magnetic attraction.

The energy transmission device 1000 is further configured and arranged to detect signals transmitted from the implantable device 100. For example, signals carrying one or more parameters and/or one or more values, may be transmitted to give feedback to the energy transmission device 1000 about the status of the implantable device 100.

It may be advantageous to use one or more signal receivers 1520 separate from the one or more energy transmitters 1550t as that allows each separate energy and signal (data) channel to be optimized separately. This is depicted in FIG. 3.

Alternatively, the one or more energy transmitters 1550t may be further configured and arranged to transmit pulse energy and/or receive signals. This is depicted in FIG. 1. Energy and data may therefore be transmitted via the same channel. The data may be received substantially simultaneously as energy pulses are transmitted, or substantially not simultaneously or overlapping in time.

Optionally, the energy transmission controller 1500 may be further configured and arranged to transmit signals to the implantable device 100. For example, signals carrying one or more parameters and/or one or more instructions, may be transmitted to instruct the implantable device 100 how, where, and when the implantable device 100 should operate. In this case, the one or more parameters and/or the one or more instructions may indicate how, where, and when the implantable device 100 should stimulate tissue.

It may be advantageous to use one or more signal transmitters, separate from the one or more energy transmitters 1550t, as that allows each separate energy and signal (data) channel to be optimized separately.

Alternatively, the one or more energy transmitters 1550t may be further configured and arranged to transmit pulse energy and/or transmit signals. Energy and data may therefore be transmitted via the same channel. The data may be transmitted substantially simultaneously as any energy pulses, or substantially not simultaneously or overlapping in time.

The one or more energy receivers 550r comprise one or more conductors, such as coils with one or more windings. They are configured to wirelessly receive pulsed energy from the associated energy transmission device 1000 when the energy transmission device 1000 is proximate. A coil with one or more windings may also be described as an inductive antenna.

It may be advantageous to embed the one or more energy receivers 550r into the substrate 300 to resist the ingress of fluids and/or a coating may be applied on top of the one or more energy receivers 550r.

An encapsulant may also be applied on top. Preferably, the encapsulant materials and properties are selected to avoid significant reduction in the energy transmission to the one or more energy receivers 550r.

FIG. 3A schematically depicts an example of a suitable pulse generator 500 or pulse energy controller. It is suitable for the embodiments described above in relation to FIG. 1. It comprises the following non-limiting examples of five main functional units:

(i) One functional unit may include one or more interfaces configured and arranged to receive electrical energy from the one or more energy receivers 550r through one or more electrical interconnection 250, and to transfer electrical energy to an energy supply regulator 501.

For example, the one or more energy receivers 550r may be disposed at a convenient position to receive energy from one or more energy transmitters 1550t (depicted in FIG. 3B).

Additionally or alternatively, one or more energy receivers 550r may be disposed at different locations in the implantable device 100.

Additionally or alternatively, one or more energy receivers 550r may be comprised within the pulse energy controller 500.

The energy transferred from the energy transmission device 100 may be provided as pulses. When received at the one or more energy receivers 500, they may be, for example, 100 microsecond to 1 millisecond wide, and repeated with 40 to 1000 Hz.

(ii) One functional unit may include an energy supply regulator 501, configured and arranged to provide suitable voltages and/or currents to energize electronic and electrical components comprised in one or more of the functional units of the pulse energy controller 500. It is further configured and arranged to provide energy, suitable for tissue stimulation, to the at least two electrodes 200a, 200b, 400a, 400b.

(iii) One functional unit may include an energy storage module 510, comprising one or more electrical and/or electronic components, configured and arranged to provide a degree of energy storage. In this example, it is comprised in the pulse generator 500. As depicted in FIG. 3A in this example, it may be comprised in the energy supply regulator 501, with a measurement connection to a control module 503.

Alternatively, the energy storage module 510 may comprise a plurality of electrical and/or electronic components, disposed at different locations within the pulse generator 500.

Additionally or alternatively, the implantable device 100 may comprise more than one energy storage module.

Additionally or alternatively, the energy storage module may be comprised in the implantable device, but external to the pulse generator 500. Additional interconnections may be required for a suitable electrical connection to the pulse generator 500.

(iv) One functional unit may include a stimulation module 502, configured and arranged to transfer energy from the energy supply regulator 501 to the at least two electrodes 200ab, 400ab, preferably as pulses. This may also be described as generating one or more stimulation pulses. In the example depicted, connections to four electrodes 200ab, 400ab are depicted.

The energy may be provided to pairs of electrodes 200a/400a and/or 200b/400b as differential potentials and/or currents.

Optionally, one or more blocking capacitors 401abcd may connected between the stimulation module 502 and one or more electrodes 200ab, 400ab to block a degree of unwanted DC component in the electrode connections. Preferably, all electrodes 200ab, 400ab are connected through a blocking capacitor to provide a high degree of safety. For example, one or more 4.7 µF (microFarad) blocking capacitors 401abcd may be used—such capacitors are available in a medical grade.

Two or more interconnections 250 are provided between the stimulation module 502 and the at least two electrodes 200ab, 400ab.

(v) One functional unit may include a control module 503, configured and arranged to control the transfer of energy from the one or more energy receivers 550r to the at least two electrodes 200ab, 400ab. It is further configured and arranged to measure parameters and/or values relevant for the execution of the method.

The interface is further configured and arranged to transmit signals to the energy transmission device 1000, as described above in relation to FIG. 1.

In this example, the one or more pulse energy receivers 550r may be further configured and arranged to receive pulse energy and/or transmit signals.

An example of an associated energy transmission device 1000 is depicted in FIG. 3B. It comprises:

one or more energy transmitters 1550t, configured and arranged to wirelessly transmit energy, as described above in relation to FIG. 1;

an energy transmission controller 1500, configured and arranged to control one or more parameters of the one or more energy transmitters 1550t, as described above in relation to FIG. 1;

an energy supply regulator 1501, configured and arranged to provide suitable voltages and/or currents to energize electronic and electrical components comprised in one or more of the functional units of the energy transmission controller 1500;

an energy storage module 1510, comprising one or more electrical and/or electronic components, configured and arranged to provide a degree of energy storage. In this example, it is comprised in the energy transmission controller 500. As depicted in FIG. 3B, in this example, it may be comprised in the energy supply regulator 1501, with a measurement connection to a control module 1503;

a wireless energy transmitter module 1504, configured and arranged to transmit energy wirelessly through the one or more energy transmitters 1550t. Preferably, the wireless energy transmitter module 1504 comprises one or more tuning components whereby to provide a high degree of efficiency (or high Q-factor or high Quality factor) during wireless energy transfer to the one or more energy receiver 550r;

a communications module 1505; and a control module 1503, configured and arranged to control the transfer of energy from the one or more energy transmitters 1550t to the implantable device 100. It is further configured and arranged to measure parameters and/or values relevant for the execution of the method.

The energy transmission device 1000 is further configured and arranged to detect signals transmitted from the implantable device 100, as described above in relation to FIG. 1.

In this example, the one or more energy transmitters 1550*t* may be further configured and arranged to transmit energy and/or receive signals.

Optionally, the energy transmission controller 1500 may be further configured and arranged to transmit signals to the implantable device 100, as described above in relation to FIG. 1.

The implantable device 100 comprises an energy storage monitor 530, configured and arranged to monitor a state of the energy storage, wherein the state is significantly affected by energy received by the implantable device 100 and/or energy used by the implantable device 100. As depicted in FIG. 3, in this example, it may be comprised in the control module 503, with a measurement connection to the energy storage module 510. It may also be advantageous to provide measurement connections to the energy supply regulator 501 and/or the stimulation module 502.

FIGS. 9A and 9B depict two views of a more detailed schematic of an example of a pulse generator 500. It comprises the same functional blocks as in FIG. 3A—however here, further details are given of examples of components and interconnections which may be used to perform those functions. The right-hand portion of FIG. 9A and the left-hand portion of FIG. 9B depict connected functional blocks, and some features are repeated in the figures to simplify the explanation below. The pulse generator 500 comprises:

- one or more energy receivers 550*r* as described above. In this example, a coil with one or more windings, configured and arranged to wirelessly receive energy from the corresponding one or more energy transmitters (not depicted), comprised in an external energy transmission device (not depicted);
- one or more tuning components 540, such as inductors and/or capacitors, to optimize the efficiency of the wireless energy transfer from the one or more energy transmitters to the one or more energy receivers 550*r*. For example, the energy may be transferred as RF with a center frequency of 13.56 MHz. As depicted in this example, the one or more tuning components 540 may be comprised in the wireless energy receiver module 504. The one or more tuning components 540 may be connected in parallel with the coil as energy receiver 550*r*;
- one or more detuning components 545. As depicted in this example, the one or more detuning components 545 are comprised in the wireless energy receiver module 504. The one or more detuning components 545 may be connected in parallel with the coil as energy receiver 550*r*. The one or more detuning components 545 are configured and arranged to provide a predetermined and/or controlled degree of "detuning" protection against "overcharging"; and
- optionally a clock recovery module 563*m*, connected, directly or indirectly to an electrical contact of the coil (as energy receiver 550*r*). The recovered clock signal 563*s*, for example 13.56 MHz, may be provided to one or more other electronic components comprised in the implantable device 100, such as a microcontroller 506. The recovered clock signal 563*s* may be used to synchronize one or more actions between the implantable device 100 and the external energy transmission device 1000. Optionally, the clock signal 563*s* may be divided, for example using a ⅟₃₂ divider.

Additionally or alternatively, this may be used to determine whether energy is being transmitted—some actions within the implantable device may be blocked when no energy is being transmitted, or blocked when energy is transmitted. For example, as transmission of data-out 566*o* uses a degree of disruption of the energy transmission channel with the modulator 565, reliable transmission of data-out 566*o* requires a degree of energy to be present in the energy transmission channel.

As will be described below, the implantable device 100 may be configured and arranged to provide three or more functions to protect against "overcharging". This may also be described as a situation in which a higher than necessary level of energy is present in the implantable device 100. The protection functions may be:

1) the implantable device 100 transmitting a sufficient energy signal to the external energy transmission device 1000. The external energy transmission device 1000 may receive the sufficient energy signal and pause energy transmissions immediately (as depicted in FIG. 4, FIG. 8, and FIG. 10). Transmission of the sufficient energy signal may be triggered when a first energy storage protection level is exceeded;

2) a degree of detuning of the energy transfer link between the one or more energy transmitters 1550*t* and the one or more energy receivers 550*r*. This may be triggered when a second energy storage protection level is exceeded;

3) a voltage regulator and/or shunt, such as one or more Zener diodes, which operates to reduce a voltage when a third energy storage protection level is exceeded;

or any combination thereof.

One, two, or three of these protection functions may be also combined with one or more further protection functions, such as:

4) the implantable device 100 transmitting an instruction to the external energy transmission device 1000 such that subsequent energy transmissions are reduced in intensity (as depicted in FIG. 2).

The implantable device 100 may be configured and arranged to provide two or more protection functions in any convenient order, allowing the protection functions to be triggered in series, in parallel, or any combination thereof. Additionally or alternatively, they may be triggered based on one or more different parameters.

The protection functions may be configured and arranged, for example:

- to reduce and/or avoid undesirable heating; and/or
- to increase or decrease the time that the implantable device 100 can operate without receiving external energy.

Minimizing the time that the implantable device may operate without receiving external energy may reduce the complexity of the implantable device (and thus the cost), may reduce the amount of energy stored (and thus the risk of overheating), and may further reduce "charging times" when energy is being stored (and thus also the risk of overheating during "charging").

Preferably, a status level is selected for monitoring, such that the status level is significantly affected by energy received by the implantable device 100 and/or energy used by the implantable device 100. The status level may be based on a single value or parameter, two or more (a plurality) values or parameters. These may be measured directly, such as a voltage, a current, a power. These may also be derived or estimated from other direct measurements.

The acceptable degree of heating may be determined by consideration of one or more parameters, such as:

implantable device 100 geometry, implantable device 100 materials, implantation depth (some devices 100 may be restricted to a maximum implantation depth), implantation location, tissue into which the implantable device 100 is implanted, the proximity of blood vessels which may provide a means of transporting heat away from the device 100, the proximity of fat tissue which may reduce the ability of surrounding tissue to transport heat away from the device 100, preference of the human or animal subject, or any combination thereof. In general, an implantable device 100 is configured and arranged to operate in an expected location and depth, or a range of locations and/or depths.

Additionally or alternatively, the acceptable degree of heating may be determined by local regulations and/or standards. For example, ISO 14708-3: 2017 Implants for surgery—Active implantable medical devices—Part 3: Implantable neurostimulators specifies that the heating of surrounding tissues should be less than two degrees Centigrade. This standard is available at the ISO.org website.

Additionally or alternatively, maximum SAR rates (Specific Absorption Rates) may also be specified, and therefore require a suitable degree of compliance.

As depicted in FIG. 9A, the one or more detuning components 545 may be connected in parallel with the coil as energy receiver 550r. This may allow a direct control of the detuning and the quality of the energy transfer—when the voltage across the coil exceeds a predetermined and/or controlled safety voltage, a predetermined and/or controlled degree of de-tuning may be applied. For example, a smaller degree of detuning may be preferred by modifying an impedance and/or a resistance connected in parallel with the coil may be modified. For example, a higher degree of detuning may be preferred by effectively "short-circuiting" the coil.

This "detuning" safety voltage is selected to correspond to the second energy storage protection level. The detuning may be for a predetermined and/or controlled period, or until particular conditions are met, or a combination thereof. Typically, detuning is performed for up to two or three ms (milliseconds).

By detuning the energy transfer link between the one or more energy transmitters 1550t and the one or more energy receivers 550r, less energy may be received by the one or more energy receivers 550r. Typically, the higher the degree of detuning, the lower the energy received. A lower degree of detuning may be preferred if the second energy storage protection level is expected to be exceeded more frequently and/or an additional protection function available. A higher degree of detuning may be preferred if the risk of overheating is to be reduced, and/or no additional protection function is available. The degree of detuning may also be dependent on the Q-factor (or Quality factor) of the energy transmission channel.

As depicted in FIG. 9A, the pulse generator 500 further optionally comprises a demodulator 560 that is configured and arranged to recover information content that has been added to the transferred energy by the external energy transmission device 1000. This information content may be extracted and passed to a suitable data decoder 561d providing a "data-in" channel 561i for the implantable device 100. As depicted in this example the demodulator 560 may be connected in parallel with the coil as the energy receiver 550r, the demodulator 560 may be comprised in the communications module 505, and/or the data decoder 561d may be comprised in the control module 503, and a modulator 565, configured and arranged to add information content to the energy transmission channel by varying one or more parameters. The external energy transmission device 1000 may be suitably configured and arranged to detect the change in the parameters of the energy transmission channel, and to recover the added information using a suitable modulator. This information may be passed from a suitable data encoder 566e to the modulator 565. This provides a "data-out" channel 566o (or data-out) for the implantable device 100. As depicted in this example the modulator 565 may be connected in parallel with the coil as the energy receiver 550r, the modulator 565 may be comprised in the communications module 505, and/or the data encoder 566e may be comprised in the control module 503. Although this may use a similar principle to detuning, the modulator 565 is preferably configured and arranged to not significantly affect energy transfer, by using a relatively small parameter variation and/or varying the parameter for a relatively short period, for example two to three microseconds (us). By using the existing energy transmission channel for providing the sufficient energy signal, complexity may be further reduced as a dedicated communication channel is not required.

As depicted in FIGS. 9A and 9B, the pulse generator 500 further comprises:

a rectifier 570, configured and arranged to convert the input alternating current (AC) 569, received by the coil as energy receiver 550r, to a direct current (DC) output 571. As depicted in this example the rectifier 570 may be connected in parallel with the coil as the energy receiver 550r; and/or the rectifier 570 may be comprised in the energy supply regulator 501.

an energy storage module 510, configured and arranged to provide a degree of energy storage in the implantable device 100. As depicted in this example, one or more buffer capacitors 510 may be provided, connected in parallel with the DC output 571 of the regulator 510. As depicted in this example, the energy storage module 510 may be comprised in the energy supply regulator 501. For example, one or more 4.7 µF (microFarad) buffer capacitors 510 may be connected in series and/or parallel—and such capacitors are available in a medical grade. For example, a voltage between 6 and 11 V may be connected across the one or more buffer capacitors 510. For example, up to one hundred 4.7 µF (microFarad) buffer capacitors 510 may be used to provide storage of up to 470 µF (microFarad).

Additionally or alternatively, one or more supercapacitors may be used as a buffer capacitor 510 and/or be comprised in the energy storage 510.

Additionally, the energy storage 510 may further comprise one or more rechargeable batteries. This is less preferred as the presence of batteries may, for example, reduce a lifetime of the implantable device 100, increase one or dimensions of the implantable device 100, increase a risk of overheating during charging, required undesired chemicals and/or substance, and/or increase complexity of the electronics. So, preferably, the energy storage 510 comprises one or more capacitors, one or more supercapacitors, or any combination thereof.

Optionally, one or more supercapacitors (or ultracapacitors) may be used. The term supercapacitor is used for any capacitor, using any technology, to provide a significantly higher degree of energy storage in packages with significantly smaller dimensions than conventional capacitors.

For some implantable devices 100, it may be preferred not to use a significant storage of energy in the energy storage 510 using electrochemistry, such as batteries and some supercapacitors, as these may require undesired chemicals and/or substance to be used.

For example, one or more buffer capacitors 510 may be configured and arranged to provide sufficient energy for correct operation during 1000 ms (milliseconds) or less, 500 ms or less, 200 ms or less, 100 ms or less, or 50 ms or less, or 20 ms or less, or 10 ms or less.

This may be predetermined and/or controlled to provide sufficient energy for at least the duration of the pause in the energy pulse transmission. In other words, the energy storage 510 may be configured and arranged to provide sufficient energy to operate the implantable device 100, whereby the duration of the pause in energy pulse transmission is 1000 ms (milliseconds) or less, 500 ms or less, 200 ms or less, 100 ms or less, 50 ms or less, 20 ms or less, or 10 ms or less.

The pulse generator 500 further comprises:
- an energy storage monitor 530, configured and arranged to monitor a state of the energy storage in the energy storage module 510. Preferably, the state is selected such that it is significantly affected by energy received by the implantable device 100 and/or energy used by the implantable device 100;
- a voltage regulator (or shunt) 575, configured and arranged to reduce a voltage when the third energy storage protection level is exceeded. As depicted in this example, one or more Zener diodes 575 are provided, connected in parallel with the DC output 571 of the regulator 510. As depicted in this example, the voltage regulator (or shunt) 575 may be comprised in the energy supply regulator 501; and
- optionally a voltage converter 577, configured and arranged to provide a DC supply 578, suitable to provide power to electronic component comprised in the implantable device 100. In this example, a DC/DC voltage converter 577 is provided connected in parallel with the DC output 571 of the regulator 510 to provide a logic voltage 578. As depicted in this example, the voltage regulator (or shunt) 575 may be comprised in the energy supply regulator 501. For example, a logic voltage 578 of 1.9V may be provided for one or more ICs such as a microcontroller 506. In this example, the microcontroller 506 is comprised in the control module 503, and controls a plurality of functions within the implantable device 100, such as communication and switching of electrodes.

As depicted in FIG. 9B, the pulse generator 500 further comprises:
- one or more electrode switching units 585abcd. Each electrode 200ab, 400ab is connected to an electrode switching unit 585abcd through one or more interconnection 250. Each switching unit 585abcd is configured and arranged to connect or disconnect the relevant stimulation electrode 200ab to/from the output voltage 571 of the rectifier 570, or connect or disconnect the relevant return electrode 400ab to/from the electrical return (not depicted). In other words, the rectifier 570 is configured and arranged to provide the relatively high voltage 571 required at the stimulation electrodes 200ab. One or more blocking capacitors 401abcd are provided to block unwanted DC current from each stimulation/return electrode pair 200/400.

Additionally or alternatively, each switching unit 585abcd is further configured and arranged to connect the relevant electrode 200ab, 400ab as either a stimulation electrode or a return electrode, for example, by using a H-bridge configuration. This provides a high degree of flexibility in determining the position and direction of stimulation energy delivery to the surrounding tissue. Optionally, each electrode 200ab, 400ab may be connected through a blocking capacitor 401abcd to provide a high degree of flexibility in determining the function of each electrode 200ab, 400ab.

As depicted in FIG. 9B, the pulse generator 500 further comprises:
- a current source 507, configured and arranged to be connected by one or more switches to one or more electrodes 200ab, 400ab. For example, a 3 mA current source. Preferably, the current source 507 is configured and arranged to monitor the current flowing, for example, by comprising a suitably configured transistor, and to pass the values on to the energy storage monitor 530; and
- a switch controller 580, configured and arranged to control the positions of one or more switches comprised in the stimulation module 501. The switch controller 580 may be comprised in the control module 503. The switch controller 580 may be controlled (not depicted) by the microcontroller 506.

For example, treatment pulses provided to the at least two electrodes 200ab, 400ab for cosmetic or therapy reasons may be 100 microsecond to 1 millisecond wide, and repeated with 40 to 1000 Hz. For treatment of pain using Peripheral Nerve Stimulation (PNS), suitable pulse parameters may be: 0-10 Volt, in particular 0.5-4.0 Volt, amplitude, 0-10 mA, 90-200 microseconds pulse width, and 50-400 Hz repetition rate.

The energy storage monitor 530 is configured and arranged to detect and/or monitor one or more parameters relating to the energy received by the implantable device 100 and/or the energy usage of the implantable device pulse energy controller 500. For example, the energy usage may be an average, maximum, or minimum value, either at a particular time or over a particular period of time. Suitable values may include energy received at the energy receivers 550r, voltage received from the energy receivers 550r at the input 569 to the rectifier 570, stimulation energy delivered through the electrodes 200ab, 400ab, stimulation voltage delivered at the output 571 of the rectifier 570, or stimulation current delivered (as measured by the current source 507). Combinations of one or more values may also be considered. Optionally, the energy storage module may also indirectly measure the tissue impedance Z(Ex-Ey) using measurements within the implantable device 100.

As depicted in FIGS. 9A and 9B, in this example, the energy storage monitor 530 may be comprised in the control module 503, with a measurement connection to the energy storage module 510. It may also be advantageous to provide measurement connections to the energy supply regulator 501 and/or the stimulation module 502.

As depicted in this example, the output DC voltage 571 of the rectifier 570 is selected as a main parameter to monitor the state of the energy storage 510. This provides a relatively direct measurement of the voltage across the buffer capacitor 510, which is affected by the voltage across the coil at the input 560 to the rectifier 570, and the energy being transferred through the electrodes 200ab, 400ab from the output 571 of the rectifier 571.

For example, where ten to fifteen volts are required at the output 571 of the rectifier 570 for the stimulation electrodes

200ab, 400ab, and approximately two volts are required for logic 578, the following examples of energy storage protection levels may be used by monitoring the rectifier output voltage 571:

1) a first energy storage protection level corresponding to a rectifier output voltage of 10.5V. If the voltage exceeds this predetermined and/or controlled value, the implantable device 100 transmits a sufficient energy signal using the data out 566o and modulator 565 to the external energy transmission device 1000;

2) a second energy storage protection level corresponding to a rectifier output voltage of 11.5V. If the voltage exceeds this predetermined and/or controlled value, the energy transfer link between the one or more energy transmitters 1550t and the one or more energy receivers 550r is detuned 545 to a predetermined and/or controlled degree;

3) a third energy storage protection level corresponding to a rectifier output voltage of 12.5V. If the voltage exceeds this predetermined and/or controlled value, the voltage is reduced using the voltage regulator (shunt) 575. Preferably, this is implemented using one or more Zener diodes;

or any combination thereof.

This example of the use of three main protection levels is schematically illustrated in FIG. 8, described in detail below.

Using all three main protection levels in this order is particularly advantageous, as using the first level (sufficient energy signal) means that the second level (detuning) is less likely to be triggered. Detuning may be disadvantageous as, in a highly detuned state, information (data) can no longer be received. In case the first and second protection levels do not work quickly enough, or are overwhelmed, the third level (Zener diodes) provides a relatively reliable and automatic protection against very high voltages. In practice, the third level may determine the maximum energy storage possible within the implantable device.

In addition, it may be advantageous to predetermine and/or control a minimum energy storage level where the implantable device properly functions. For example, if less than two volts, logic functions will not operate correctly. As another example, if above two volts, but below nine volts, the one or more electrical stimulation pulses provided to the electrodes 200ab, 400ab may be distorted. In this example, a minimum voltage of nine volts at the output 571 of the rectifier 570 may be used.

FIG. 2 schematically depicts examples of the data (signal) communication and energy transmission signals generated when carrying out a first method of controlling the wireless energy transfer from the energy transmission device 1000 to the wireless implantable device 100.

A series of waveforms are depicted from top to bottom: the energy transmitted 1550e by the energy transmission device 1000, the energy received 550e at the implantable device 100, the level of energy stored 510e in the energy storage module 510m, and data-out 566o transmitted by the implantable device 100. The data-out 566o may be used to provide feedback. Signals and/or pulses that are at the same horizontal position occur substantially simultaneously. Time runs from left to right, from t0 to t9. The amplitude of each pulse represents a power value, and the area under each pulse represents the energy.

Energy is transmitted 1550e as a plurality of successive energy pulses having varying amplitudes or power levels). In this context, plurality means two or more.

On the left-hand-side (time=0 or t0), energy transmitted 1550e starts at approximately zero.

In this example, the energy storage monitor 530 is configured and arranged to monitor the energy level 510e of the energy storage module 510m, and to take action if an energy storage upper limit 515 is exceeded and/or if the energy level drops below an energy storage lower limit 514.

In this case, energy 1550e is transmitted regularly over the entire time period depicted to charge 510e the energy storage module 510m and to keep it charged 510e within the energy storage upper limit 515 and energy storage lower limit 514. The period of the transmitted pulses 1550e is t1 to t3 (which is approximately equal to t3 to t5 and approximately equal to t5 to t7. The duty cycle is approximately 50%.

As depicted in this example, the energy transmission device 1000 is configured and arranged to provide the energy in pulses as this may provide a better degree of control, especially in an initial start-up phase for the implantable device 100. Subsequently or alternatively, energy may be supplied continuously until the implantable device signals that the transmission should be adapted, or until the maximum energy storage situation is reached.

Pulse [a] of the transmitted energy 1550e is the first pulse to occur, and it starts on the left-hand side, from t1 to t2, with an initial amplitude or power level 1552. Substantially simultaneously, a pulse [b] of energy is received 550e by the implant, from t1 to t2.

In this example, the level of the energy storage 510e at t=0 is assumed to be equal to the energy storage lower limit 514. Because the energy storage level is less than the energy storage upper limit 515, the implantable device 100 allows at least a portion of the energy received 550e to charge the energy storage module 510m. As depicted, between t1 and t2, the level of the energy storage 510e rises in section [c] from the energy storage lower limit 514 upwards.

Between the pulses [a] and [e] of transmitted energy 1550e, from t2 to t3, the transmitted energy is approximately zero. It is assumed that the implantable device 100 uses/loses a portion of the stored energy 510e, so the curve in section [d] declines.

The pulse [e] of the transmitted energy 1550e is the second pulse to occur, from t3 to t4. As no feedback was sent by the implantable device 100 during the last cycle, the energy transmission device 1000 continues—and the energy transmission device 1000 transmits a pulse [e] with approximately the same amplitude or power level 1552 (in other words, at the initial amplitude or power level 1552) and duration as the first pulse [a]. Substantially simultaneously, a pulse [f] of energy is received 550e by the implant, from t3 to t4.

Because the energy storage 510e energy level is less than the energy storage upper limit 515, the implantable device 100 allows at least a portion of the energy received 550e to further charge the energy storage 510e. As depicted, between t3 and t4, the level of the energy storage 510e rises in section [g] upwards.

At time tx, between t3 and t4, the energy storage level 510e becomes the same as the energy storage upper limit 515. At that moment, the energy storage monitoring 530 generates a signal [h], which is transmitted as data-out 566o from the implantable device 100 to the external energy transmission device 1000. This signal is preferably sent when there is sufficient energy in the energy transmission channel. This signal [h] preferably provides additional information, such as the rate of increase, to allow the energy transmitting device 1000 to decide on the most appropriate remedial action.

Additionally or alternatively, the implantable device 100 may decide the most appropriate remedial action, and instruct the external energy transmission device 1000 to carry it out.

As the energy 1550e was still being transmitted between tx and t4, the energy storage level 510e exceeds the energy storage upper limit 515 at t4.

Between the pulses [a] and [e] of transmitted energy 1550e, from t4 to t5, the transmitted energy is approximately zero. It is assumed that the implantable device 100 uses/loses a portion of the stored energy 510e, so the curve in section [j] declines.

The pulse [k] of the transmitted energy 1550e is the third pulse to occur, from t5 to t6. As feedback was sent by pulse [h] during the last cycle, the energy transmission device 1000 transmits a pulse [k] with a significantly reduced amplitude or power level 1553 compared to the second pulse [e]. Substantially simultaneously, a pulse [1] of energy is received 550e by the implant, from t5 to t6.

The energy received 550e by the implantable device 100 is used to further charge the energy storage of the implantable device 100—however, it is assumed that the implantable device 100 uses/loses a portion of the stored energy 510e, so the curve in section [j] goes down, but at a reduced rate due to the received energy 550e in pulse (1).

Between the pulses [k] and [p] of transmitted energy 1550e, from t6 to t7, the transmitted energy is approximately zero. It is assumed that the implantable device 100 uses/loses a portion of the stored energy 510e, so the curve in section [n] declines. The pulse of the transmitted energy 1550e is the fourth pulse to occur, from t7 to t8. As feedback was sent by pulse [h] two cycles earlier, the energy transmission device 1000 transmits a pulse with approximately the same amplitude or power level 1553 (in other words, at the significantly reduced amplitude or power level 1553) and duration as the third pulse Pa Substantially simultaneously, a pulse [q] of energy is received 550e by the implant, from t7 to t8.

The energy received 550e by the implantable device 100 is used to further charge the energy storage of the implantable device 100—however, it is assumed that the implantable device 100 uses/loses a portion of the stored energy 510e, so the curve in section [r] goes down, but at a reduced rate due to the received energy 550e in pulse (q).

After pulse of transmitted energy 1550e, from t8 to t9, the transmitted energy is approximately zero. It is assumed that the implantable device 100 uses/loses a portion of the stored energy 510e, so the curve in section [s] declines further.

The level of energy 510e in the energy storage module 510m eventually falls below (not depicted) the energy storage lower limit 514. At that moment, the energy storage monitoring 530 generates a signal (not depicted), which is transmitted as data-out 566o from the implantable device 100 to the external energy transmission device 1000. This signal preferably provides additional information, such as the rate of decrease, to allow the energy transmitting device 1000 to decide on the most appropriate remedial action. This signal is preferably sent when there is sufficient energy in the energy transmission channel.

Additionally or alternatively, the implantable device 100 may decide the most appropriate remedial action, and instruct the external energy transmission device 1000 to carry the remedial action out.

From that point, the cycle will begin again from t0.

It may be advantageous to apply hysteresis if the energy storage upper limit 515 and the energy storage lower limit 514 are close together.

Although this first method of controlling energy transfer may be advantageous for certain embodiments, there may be other embodiments where it is less advantageous. For example, the remedial actions, such as reducing the amplitude (power), may take a relatively long time to have an effect, allowing the temperature of the implantable device to become undesirably high;

generation of the feedback signal as a data-out 566o may require relatively complicated electronics. These may increase the costs and size of the implantable device 100;

a variable amplitude/power transmitter is required, increasing complexity of the energy transmission device 1000;

deciding on the appropriate remedial action may also require relatively complicated electronics in the implantable device 100 and/or in the energy transmission device 1000. Especially for medical implants, it may be undesirable for the implantable device 100 to be solely dependent on an external device 1000 for correct operation;

frequently, the energy transmitted is more than required, increasing the risk of undesirable heating.

FIG. 4 schematically depicts examples of the data (signal) communication and energy transmission signals generated when carrying out a second method of controlling the wireless energy transfer from the energy transmission device 1000 to the wireless implantable device 100.

A series of waveforms are depicted from top to bottom: the energy transmitted 1550e by the energy transmission device 1000, the energy received 550e at the implantable device 100, the level of energy stored 510e in the energy storage module 510m, and a sufficient energy signal transmitted as data-out 566o by the implantable device 100. Signals and/or pulses that are at the same horizontal position occur substantially simultaneously. Time runs from left to right, from t0 to t9. The amplitude of each pulse represents a power value, and the area under each pulse represents the energy.

Energy is transmitted 1550e as a plurality of successive energy pulses having substantially the same amplitude (or power)—in other words, at first amplitude (or power) level 1551. In this context, plurality means two or more. The period of the transmitted pulses 1550e is t1 to t3 (which, in this example is approximately equal to t3 to t5, and approximately equal to t5 to t7). The duty cycle in period t1 to t3 is initially approximately 50%.

On the left-hand-side (time=0 or t0), energy transmitted 1550e starts at approximately zero.

In this example, the energy storage monitor 530 is configured and arranged to monitor the level of the energy storage 510e, and to take action if the level 510e exceeds a first energy storage protection level 511.

In this case, energy 1550e is transmitted regularly over the entire time period depicted to charge the energy storage 510e and to keep it charged as close as possible to the first protection level 511. As in FIG. 2, the energy is transmitted in pulses. However, in this second method depicted in FIG. 4, the amplitude (power) of the transmitted energy pulses 1550e remains substantially the same—however, the duration of the pulses (or duty cycle) may vary.

The pulse [a] of the transmitted energy 1550e is the first pulse to occur, and it starts on the left-hand side, from t1 to t2. Substantially simultaneously, a pulse [b] of energy is received 550e by the implant, from t1 to t2.

In this example, the level of the energy storage 510e at t=0 is assumed to be below the first energy storage protection level 511. Because the energy storage level 510e is less than the first protection level 511, the implantable device 100 allows at least a portion of the energy received 550e to charge the energy storage module 510*m*. As depicted, between t1 and t2, the level of the energy storage 510*e* rises upwards in section [c].

Between the pulses [a] and [e] of transmitted energy 1550*e*, from t2 to t3, the transmitted energy is approximately zero. It is assumed that the implantable device 100 uses/loses a portion of the stored energy 510*e*, so the curve in section [d] declines.

The pulse [e] of the transmitted energy 1550*e* is the second pulse to occur, from t3 to t4. As no feedback was sent by the implantable device 100 during the last cycle, the energy transmission device 1000 continues—it transmits a pulse [e] with approximately the same duration as the first pulse [a]. Substantially simultaneously, a pulse [f] of energy is received 550*e* by the implant, from t3 to t4.

Because the energy storage 510*e* level is less than the first energy storage protection level 511, the implantable device 100 allows at least a portion of the energy received 550*e* to further charge the energy storage 510*e*. As depicted, between t3 and t4, the level of the energy storage 510*e* rises upwards in section [g].

At time tx, between t3 and t4, the energy storage level 510*e* becomes the same as the first energy storage protection level 511. At that moment, the energy storage monitoring 530 generates a sufficient energy signal [h], which is transmitted as data-out 566*o* from the implantable device 100 to the external energy transmission device 1000. This sufficient energy signal [h] is a signal, intended as a request to energy transmitting devices to pause transmission. This may be of a predetermined and/or controlled duration and this may be advantageous in reducing power usage, particularly when the implantable device comprises additional protection functions.

Alternatively, the sufficient energy signal may be sent until the energy received 550*e* falls below a predetermined and/or controlled level.

Upon receipt of the sufficient energy signal, the energy transmitter 1550*t* immediately stops transmitting pulses 1550*e*, with the intention to resume transmission after a pause.

In this context, "immediately" means "as soon as possible". For example:
- less than 2 ms (milliseconds) after receiving the sufficient energy signal [h], or
- less than 1 ms (millisecond) after receiving the sufficient energy signal [h], or
- less than 100 us (microseconds) after receiving the sufficient energy signal [h], or
- less than 10 us (microseconds) after receiving the sufficient energy signal [h].

This may also be described as a stopping time. It may be advantageous to predetermine and/or control the stopping time to be as small as possible as this reduces the risk that the implantable device 100 receives too much energy. Preferably, the energy transmission device 1000 may be configured and arranged to keep the latency (e.g., lag) relatively low in stopping the transmission of pulses after receipt of the sufficient energy signal. For example, this may be accomplished by including one or more dedicated components and/or a dedicated circuit.

The energy transmitter 1550*t* does not always continue until the scheduled end of the pulse being transmitted 1550*e*. If the remaining duration of the pulse being transmitted 1550*e* is less than or equal to the stopping time, the pulse being transmitted 1550*e* will appear to end as scheduled. In other words, the duty cycle in such a period was initially scheduled to be approximately 50%, and remains approximately 50%.

If the remaining duration of the pulse being transmitted 1550*e* is greater than the stopping time, the pulse being transmitted 1550*e* will be truncated. For example, the truncated duration may be less than the scheduled duration. As depicted, the energy transmission pulse [e] is truncated, and therefore shorter in time than pulse [a] by t4-ty. In other words, in this case, the duty cycle in period t3 to t5 was initially scheduled to be approximately 50%, but becomes approximately 44.5% due to the truncation.

This sufficient energy signal [h] is preferably sent when there is sufficient energy in the energy transmission channel.

As the energy 1550*e* was still being transmitted between tx and t4, the energy storage level 510*e* continues to rise, and further exceeds the first energy storage protection level 511 at t4.

Between the pulses [e] and [k] of transmitted energy 1550*e*, from t4 to t5, the transmitted energy is approximately zero. It is assumed that the implantable device 100 uses/loses a portion of the stored energy 510*e*, so the curve in section [j] declines.

The pulse [k] of the transmitted energy 1550*e* is the third pulse to occur, intended to be from t5 to t6. As the energy transmission device 1000 is configured and arranged to keep transmitting energy unless a sufficient energy signal is received, a pulse [k] is transmitted with substantially the same amplitude (power) as the previous pulses [a] and [e]—in other words, at the first amplitude (or power) level 1551. Substantially simultaneously, a pulse [1] of energy is received 550*e* by the implant.

During this pulse [k] and [1], the energy storage 510*e* level exceeds the first energy storage protection level 511. At that moment, the energy storage monitoring 530 generates a sufficient energy signal [n], which is transmitted as data-out 566*o* from the implantable device 100 to the external energy transmission device 1000. This sufficient energy signal [n] is a signal, signifying a request to pause.

Upon receipt of the sufficient energy signal, the energy transmitter 1550*t* "immediately" pauses transmitting as before. This sufficient energy signal [n] is preferably sent when there is sufficient energy in the energy transmission channel. The energy transmission pulse [k] is therefore shorter in time than pulse [a] by t6-tz. In other words, in this case, the duty cycle in period t5 to t7 was initially scheduled to be approximately 50%, but becomes approximately 10.5% due to the truncation.

As the energy 1554 was still being transmitted between t5 and tz, the energy storage level 510*e* continues to rise a little, and further exceed the first energy storage protection level 511.

Between the pulses [k] and [q] of transmitted energy 1550*e*, from tz to t7, the transmitted energy is approximately zero. It is assumed that the implantable device 100 uses/loses a portion of the stored energy 510*e*, so the curve in sections [m] and [p] go down.

The pulse [q] of the transmitted energy 1550*e* is the fourth pulse to occur, intended to be from t7 to t8. As the energy transmission device 1000 is configured and arranged to keep transmitting energy unless a sufficient energy signal is received, a pulse [k] is transmitted with substantially the same amplitude (power) 1551 as the previous pulses [a], [e] and [k]—in other words, at the first amplitude (or power) level 1551. Substantially simultaneously, a pulse [r] of energy is received 550*e* by the implant.

During this pulse [q] and [r], the energy storage 510*e* level exceeds the first energy storage protection level 511. At that moment, the energy storage monitoring 530 generates a sufficient energy signal [s], which is transmitted as data-out 566*o* from the implantable device 100 to the external energy transmission device 1000. This sufficient energy signal [s] is a signal, signifying a request to pause.

Upon receipt of the sufficient energy signal, the energy transmitter 1550*t* "immediately" pauses transmitting as before. This sufficient energy signal [s] is preferably sent when there is sufficient energy in the energy transmission channel. The energy transmission pulse [q] is therefore shorter in time than pulse [a] by t8-tw. In other words, in this case, the duty cycle in period starting at t7 was initially scheduled to be approximately 50%, but becomes approximately 25% due to the truncation. As the energy 1550*e* was still being transmitted between t7 and t8, the energy storage level 510*e* continues to rise a little, and further exceed the first energy storage protection level 511.

After pulse [q] of transmitted energy 1550*e*, after tw, the transmitted energy is approximately zero. It is assumed that the implantable device 100 uses/loses a portion of the stored energy 510*e*, so the curve in sections [t] and [u] declines.

This second method of controlling energy transfer may be advantageous for certain embodiments compared to the first method, depicted in FIG. 2. This reduces the risk that the temperature of the implantable device becomes undesirably high. In particular:

- remedial actions are triggered by a similar, sometimes identical, signal from the implantable device 100;
- generation of such a feedback signal [h], [n], [s] only requires simpler electronics, further reducing the required complexity of the implantable device 100;
- a fixed power transmitter may be used, reducing complexity of the energy transmission device 1000;
- remedial actions performed by the external power transmitter 1000 including a similar, sometimes identical—pausing transmission of the energy pulses 1550*e* as soon as possible;
- energy transfer control may be performed with limited or even no handshaking protocols. Especially for medical implants, it is advantageous that the implantable device 100 has a high degree of independence from external devices 1000 for correct operation. Also, little or no handshaking may reduce the communication overhead, further increasing the speed of response by the energy transmission device 1000; and
- the energy transmitted is optimized, reducing the risk of undesirable heating by mainly transmitting energy when needed.

In addition, by allowing the energy transmission to be paused by truncating the current pulse 1550*e* (if applicable), the risk of overheating may be further reduced. This may be advantageous compared to devices where amplitude or power levels are continuously varied following comparisons with the desired settings required by a patient. The methods in this disclosure differ from known devices which provide feedback about their status—conventionally, reporting a ready state may be considered a request to start and/or continue energy transmission. This is not the same as a request to pause.

FIG. 8 schematically depicts the use of one, two or three main protection levels. Examples of data (e.g., signal) communication and energy transmission signals generated are depicted when carrying out further methods of controlling the wireless energy transfer from the energy transmission device 1000 to the wireless implantable device 100.

A series of waveforms are depicted from top to bottom: the energy transmitted 1550*e* by the energy transmission device 1000, a sufficient energy signal transmitted as a data out 566*o* by the implantable device 100, and the level of energy stored 510*e* in the energy storage module 510*m*. Signals and/or pulses that are at the same horizontal position occur substantially simultaneously. Time runs from left to right, from t0 to t9, and depicts three different possible protection steps a, b, and c are depicted from left to right. The amplitude of each pulse represents a power value, and the area under each pulse represents the energy.

Protection step a is the same as the protection described above in relation to the period between t3 and t4 in FIG. 4.

Energy is transmitted 1550*e* as a plurality of successive energy pulses having substantially the same amplitude or power level 1551—in other words, at the first amplitude (or power) level 1551. In this context, plurality means two or more. In this case, the period is approximately constant, and the scheduled duty cycle is approximately 74%.

In this example, the energy storage monitor (not depicted) is configured and arranged to monitor the level of the energy storage 510*e*, and to take action if the level 510*e*:

- exceeds a first energy storage protection level 511. For example, as described above in relation to FIGS. 9A and B, a rectifier output voltage of 10.5V;
- exceeds a second energy storage protection level 512. For example, as described above in relation to FIGS. 9A and B, a rectifier output voltage of 11.5V; and
- exceeds a third energy storage protection level 513. For example, as described above in relation to FIGS. 9A and B, a rectifier output voltage of 12.5V; In this case, energy 1550*e* is transmitted regularly over the entire time period depicted to charge the energy storage 510*e* and to keep the energy storage 510*e* charged as close as possible to the first protection level 511. As in FIG. 4, the energy is transmitted in pulses and the amplitude or power level 1551 of the transmitted energy pulses 1550*e* remains substantially the same—in other words, at a first amplitude (or power) level 1551. However, the duration of the pulses (e.g., duty cycle) may vary. The energy transmission device 1000 is configured and arranged to take suitable actions to immediately pause the transmission of energy 1550*e* through the one or more energy transmitters 1550*t* when the energy transmission device 1000 receives a sufficient energy signal from the implantable device 100. In this example, during a period of operation, the time between the start of the transmitted pulses 1550*e* (or period) remains substantially the same.

A pulse of the transmitted energy 1550*e* is the first pulse to occur, and the pulse starts on the left-hand side. Substantially simultaneously, a pulse of energy is received by the implant (not depicted) and passed on to the energy storage module 510*m*.

In this example, the level of the energy storage 510*e* is assumed to be below the first energy storage protection level 511. Because the energy storage level 510*e* is less than the first energy storage protection level 511, the implantable device 100 allows at least a portion of the energy received to charge the energy storage 510*e* and the level of the energy storage 510*e* rises upward.

At time t0, the energy storage level 510*e* becomes the same as the first energy storage protection level 511. At that moment, the energy storage monitoring (not depicted) generates a sufficient energy signal, which is transmitted as data-out 566*o* from the implantable device 100 to the external energy transmission device 1000. This sufficient energy signal [h] is a signal, signifying a request to pause.

In this example, the implantable device 100 is configured and arranged to send a sufficient energy signal as data-out 566o until the energy received falls below a predetermined and/or controlled level. This may be advantageous when the implantable device either does not comprise additional protection functions, or the implantable device 100 is preferred not to use additional protections due to the serious disruption to normal operation.

Alternatively, the sufficient energy signal may be of a predetermined and/or controlled duration.

At time t1, the sufficient energy signal as data-out 566o is detected by the energy transmission device 1000. This may be almost simultaneously. Alternatively, as depicted in the example, there may be a delay. This delay may be influenced by one or more parameters which may include: distance between the implantable device 100 and the energy transmission device 1000, the type of tissue between the implanted device and the energy transmission device, one or more alignment angles, the power of the sufficient energy signal, the transmission power of the data-out channel 566o, the sensitivity of the detection by the energy transmission device 1000, the time to decrypt or decode the sufficient energy signal, distortion of the sufficient energy signal, or any combination thereof.

Upon receipt of the sufficient energy signal as data-out 566o, the energy transmission device 1000 takes suitable actions to immediately pause the transmission of energy through the one or more energy transmitters 1550t. As depicted, the energy transmission 1550e ends at t2.

As depicted in the example, the scheduled remaining duration (until t3) of the pulse being transmitted 1550e is greater than the stopping time, so the pulse being transmitted 1550e will be truncated, the truncated duration being less than the scheduled duration. For example, as depicted, the energy transmission pulse is truncated by t3–t2. In other words, in this case, the duty cycle in the first period was initially scheduled to be approximately 74%, but becomes approximately 54.5% due to the truncation.

As the energy 1550e was still being transmitted between t0 and t2, the energy storage level 510e continues to rise, and further exceeds the first energy storage protection level 511. However, once transmitted energy 1550e is low or approximately zero (from t2), the implantable device 100 uses/loses a portion of the stored energy 510e, so the energy storage level 510e goes down below the first energy storage protection level 511. When the implantable device 100 determines that the energy storage level 510e falls below the first energy storage protection level 511, the implantable device 100 stops transmitting the sufficient energy signal as data-out 566o.

As the energy transmission device 1000 is configured and arranged to keep transmitting energy unless a sufficient energy signal is received, a second pulse 1550e is transmitted with substantially the same amplitude or power level 1551 as the previous first pulse—in other words, at the first amplitude (or power) level 1551. Because the energy storage level 510e is less than the first protection level 511, the implantable device 100 allows at least a portion of the energy received to charge the energy storage 510e and the level of the energy storage 510e rises upward.

At time t4, the energy storage level 510e again becomes the same as the first energy storage protection level 511. At that moment, the implantable device 100 generates a sufficient energy signal, which is transmitted as data-out 566o. In this example, the implantable device 100 is still configured and arranged to send a sufficient energy signal until the energy received falls below a predetermined and/or controlled level.

As depicted in the example, the implantable device 100 has been configured and arranged to implement a further protection step b. For this protection step, different to the situation described above for step a, it is assumed that the energy transmission device 1000 does not receive and/or does not recognize the sufficient energy signal from the implantable device 100.

This may be due to a change in one or more parameters, which may include: an increase in the distance between the implantable device 100 and the energy transmission device 1000 due to migration or physical movement, an increase in one or more alignment angles due to migration or physical movement, a defect in the implantable device 100 and/or energy transmission device 1000, a distortion or disturbance in the sufficient energy signal, a distortion or disturbance in the data-out channel 566o, or any combination thereof.

So, although the implantable device 100 had expected the energy transmission device 1000 to receive the sufficient energy signal at t5, the transmission device 1000 does not take suitable actions to immediately pause the transmission of energy 1550e through the one or more energy transmitters 1550t. As depicted, the energy transmission in the second pulse 1550e is not truncated, and ends as scheduled by the transmission device 1000. In other words, in this case, the duty cycle in the second period was initially scheduled to be approximately 74%, and remains approximately 74% due to the lack of suitable actions.

The implantable device 100 continues to send a sufficient energy signal as data-out 566o because the energy stored is above the first energy storage protection level 511.

As the energy 1550e is still being transmitted after t4 and after t5, the energy storage level 510e continues to rise, and further exceeds the second energy storage protection level 512 at t6. The implantable device 100 is configured and arranged to provide a degree of detuning of the energy transfer link between the one or more energy transmitters 1550t and the one or more energy receivers.

As described above, the detuning may be for a predetermined and/or controlled period, until particular conditions are met, or a combination thereof. The higher the degree of detuning, the lower the energy that may be received in the implantable device 100. and the lower the energy being supplied to the energy storage level 510e.

The degree of detuning may be kept small and/or brief as the energy transfer link may also be used for communication. If a lower risk of overheating is preferred, a higher degree of detuning may be predetermined and/or controlled. In the example depicted in FIG. 8, some energy is still received, so the energy storage level 510e continues to rise, and further exceeds the second energy storage protection level 512. In this example, a lower degree of detuning is predetermined and/or controlled because a further protection step c is available.

However, once transmitted energy 1550e is low or approximately zero (after the end of the scheduled transmission), the implantable device 100 uses/loses a portion of the stored energy 510e, so the energy storage level 510e goes down. In the example depicted in FIG. 8, the energy storage level 510e stays above the second energy protection level 512.

The implantable device 100 continues to send a sufficient energy signal as data-out 566o because the energy stored is above the first energy storage protection level 511. The implantable device 100 further continues to provide a degree of detuning of the energy transfer link because the energy stored is above the second energy storage protection level 512.

As the energy transmission device 1000 is configured and arranged to keep transmitting energy unless a sufficient energy signal is received, and the sufficient energy signal is not received and/or not recognized, a third pulse 1550e is transmitted with substantially the same amplitude (power) 1551 as the previous first and second pulses 1550e starting at t7—in other words, at the first amplitude (or power) level 1551.

As depicted in the example, the implantable device 100 has been configured and arranged to implement a further protection step c. For this protection step, it is different to the situation described above for step b. In this case, it is further assumed that the degree of detuning applied by implantable device 100 is insufficient to prevent a further rise in the energy storage level 510e.

This may be due to a change in one or more parameters, which may include: a greater than expected transmission power level, simultaneous exposure to a further energy transmission device, an increase in environmental or background energy, a defect in the implantable device 100 and/or energy transmission device 1000, or any combination thereof.

In the example depicted in FIG. 8, the source of the received energy is assumed to be the energy transmission device 1000, which does not take suitable action to immediately pause the transmission of energy. As the energy 1550e is still being transmitted after t7, the energy storage level 510e continues to rise.

The implantable device 100 continues to send a sufficient energy signal as data-out 566o because the energy stored is above the first energy storage protection level 511. The implantable device 100 further continues to provide a degree of detuning of the energy transfer link because the energy stored is above the second energy storage protection level 512.

As the energy storage level 510e continues to rise, it exceeds the third energy storage protection level 513 at t8. The implantable device 100 is configured and arranged to reduce the energy storage level 510e from further increases by modifying one or more voltage regulators and/or operating one or more shunts. For example, as described above, one or more Zener diodes may be used.

After t8, the energy storage level 510e remains at the level determined by the voltage regulator and/or shunt. In the example depicted, the energy storage level 510e does not exceed the third energy storage level 513.

The energy transmission device 100 continues to transmit the third pulse 1550e as scheduled with substantially the same amplitude (power) 1551 as the previous first and second pulses 1550e (in other words, at the first amplitude or power level 1551), and ends the scheduled pulse at t9. However, the energy storage level 510e remains at the third energy storage level 513. In other words, in this case, the duty cycle in the third period was initially scheduled to be approximately 74%, and remains approximately 74% due to the lack of suitable actions.

Once transmitted energy 1550e is low or approximately zero (after the end of the scheduled transmission t9), the implantable device 100 uses/loses a portion of the stored energy 510e, so the energy storage level 510e goes down.

In the example depicted in FIG. 8, the implantable device 100 is configured and arranged to provide one, two, or three protection steps a, b and/or c. In some configurations, it may be sufficient to only have a, to have a and b, or to have a and c. This may also be at least partially determined by local regulations and/or standards. As explained above, the protection steps may also be configured to operate in a different order, such as bac, bca, cba, cab, or acb.

One or more additional protection steps may also be implemented, such as transmitting an instruction to the external energy transmission device 1000 such that subsequent energy transmissions are reduced in intensity (as depicted in FIG. 2).

For example, in some configurations, energy transmission channel may be detuned to a high degree for longer periods of time. However, this effectively reduces energy received in the implantable device 100 to shorter bursts of energy, thereby reducing heating of the implantable device 100.

FIG. 10 schematically depicts still further methods of controlling the wireless energy transfer from the energy transmission device 1000 to the wireless implantable device 100 using at least one protection function.

A series of waveforms are depicted from top to bottom: the energy transmitted 1550e by the energy transmission device 1000, a modified sufficient energy signal as modified data-out 2566o transmitted by the implantable device 100, and the level of energy stored 510e in the energy storage module 510m. Signals and/or pulses that are at the same horizontal position occur substantially simultaneously. Time runs from left to right, from t0 to t10. The amplitude of each pulse represents a power value, and the area under each pulse represents the energy.

Energy is transmitted 1550e as a plurality of successive energy pulses having substantially the same amplitude (or power) 1551—in other words, at a first amplitude or power level 1551. In this context, plurality means two or more. In this case, the period and/or scheduled duty cycle may be varied.

In this example, the energy storage monitor (not depicted) is configured and arranged to monitor the level of the energy storage 510e, and to take action if the level 510e exceeds a first energy storage protection level 511. For example, as described above in relation to FIGS. 9A and B, a rectifier output voltage may be 10.5V. This is the same protection as described above in relation to the period between t3 and t4 in FIG. 4, and protection step a in FIG. 8.

Optionally, one or more energy storage protection levels are monitored, but these are not depicted.

In this case, energy 1550e is transmitted regularly over the entire time period depicted to charge the energy storage 510e and to keep it charged as close as possible to the first protection level 511. As in FIG. 4 and FIG. 8, the energy is transmitted in pulses. and the amplitude (power) 1551 of the transmitted energy pulses 1550e remains substantially the same (in other words, at the first amplitude or power level 1551)—however, the duration of the pulses (or duty cycle) may vary.

The energy transmission device 1000 is configured and arranged to take suitable actions to immediately pause the transmission of energy 1550e through the one or more energy transmitters 1550t when it receives a modified sufficient energy signal as modified data-out 2566o from the implantable device 100. In this example, during a period of operation, the time between the start of transmitted pulses 1550e (or period) may be variable.

In this example, the implantable device 100 is configured and arranged to send a modified sufficient energy signal as modified data-out 2566o if the energy stored is above the first energy storage protection level 511. The modified sufficient energy signal and the modified data-out 2566*o* are the same as the sufficient energy signal and data-out 566*o* described above, except for:

- it has a duration which is predetermined and/or controlled. In the example depicted in FIG. 10, each modified sufficient energy signal has substantially the same duration; and
- the implantable device 100 is further configured and arranged to transmit the modified sufficient energy signal as modified data-out 2566*o* modulated around two or more different frequencies. For example, as depicted in the example of FIG. 10, two types of modified sufficient energy signal are depicted—an "a-type" modified sufficient energy signal modulated around a first frequency, for example approx. 212 kHz, and a "b-type" modified sufficient energy signal modulated around a second frequency, for example approx. 424 kHz. Any frequency combinations, and any number of separate frequencies, may be used that are distinguishable by the energy transmission device 1000.

The use of a modified sufficient energy signal as modified data-out 2566*o* allows the implantable device 100 to provide a further communication channel to the energy transmission device 1000. This may be advantageous as the further communication channel may be less sensitive to the Q-factor (or Quality factor) of the energy transmission channel.

For example, in a simple encoding, an "a-type" signal as modified data-out 2566*o* may be considered as a "0" bit and a "b-type" signal as modified data-out 2566*o* as a "1" bit, allowing encoded data to be sent using one or more modified sufficient energy signals. This communication may be used to control, or provide feedback on, one or more parameters of the energy transmission, which includes:

a default transmission pulse 1550*e* duration; a pause duration until the next transmission pulse 1550*e* should be sent, a default amplitude or power level to be used for a plurality of energy transmission pulses 1550*e*, feedback regarding a quality of energy transfer, feedback regarding a quality of any data transmission from the energy transmission device 1000, an energy storage status, an indication of health of the implantable device 100, or any combination thereof.

In general, it may be advantageous to simplify the additional data and/or information being sent using the modified sufficient energy signal as modified data-out 2566*o*. In many configurations, the primary function of the modified sufficient energy signal is to cause the energy transmission to be paused, and the addition of additional complexity to transmit the additional information and/or data is undesired because it may reduce the reliability of the primary function. In other configurations, this trade-off may be more acceptable.

Communication may be further simplified by providing relative instructions, such as "longer", "shorter", 10% longer, and 10% shorter, among others.

It may also be advantageous for an implantable device 100 to comprise one or more sensors for measuring one or more values within the implantable device 100, and/or one or more values in the environment adjacent to the implantable device 100, and/or one or more values relating to the intended operation of the implantable device 100. The modified sufficient energy signal as modified data-out 2566*o* may be used to provide at least a part of this measurement data to the energy transmission device 1000.

In the example depicted in FIG. 10, the implantable device 100 is configured and arranged such that an "a-type" sufficient energy signal as modified data-out 2566*o* is sent as a request that the transmitting energy be paused for a standard duration "c", and a "b-type" sufficient energy signal as modified data-out 2566*o* is sent as a request that the transmitting energy be paused for a longer-than-standard duration "d".

A pulse of the transmitted energy 1550*e* is the first pulse to occur, and the transmitted energy may start on the left-hand side. Substantially simultaneously, a pulse of energy is received by the implant (not depicted) and passed on to the energy storage module 510*m*.

In this example, the level of the energy storage 510*e* is assumed to be below the first energy storage protection level 511. Because the energy storage level 510*e* is less than the first protection level 511, the implantable device 100 allows at least a portion of the energy received to charge the energy storage 510*e* and the level of the energy storage 510*e* rises upward.

At time t0, the energy storage level 510*e* becomes the same as the first energy storage protection level 511. At that moment, the energy storage monitoring (not depicted) generates an "a-type" modified sufficient energy signal, which is transmitted as modified data-out 2566*o* from the implantable device 100 to the external energy transmission device 1000. This modified sufficient energy signal "a-type" is a signal, signifying a request to pause.

In this example, the implantable device 100 is configured and arranged to send a modified sufficient energy signal as modified data-out 2566*o* of a predetermined and/or controlled duration. This may be advantageous to reduce power usage, particularly when the implantable device comprises additional protection functions.

Alternatively, the implantable device 100 may be configured and arranged to send a modified sufficient energy signal using modified data-out 2566*o* until the energy received falls below a predetermined and/or controlled level.

The modified sufficient energy signal as modified data-out 2566*o* is detected by the energy transmission device 1000 and the energy transmission device 1000 takes suitable actions to immediately pause the transmission of energy 1550*e* through the one or more energy transmitters 1550*t*. As depicted, the energy transmission 1550*e* ends at t1. Additionally, the energy transmission device 1000 recognizes the modified sufficient energy signal 2566 as an "a-type"—the energy transmission device 1000 is configured and arranged to transmit the next pulse after pause duration "c".

In the example, the scheduled remaining duration (not depicted) of the pulse being transmitted 1550*e* is greater than the stopping time, so the pulse being transmitted 1550*e* will be truncated at t1, the truncated duration being less than the scheduled duration. The energy transmission device 1000 schedules the next pulse to be transmitted at t1+"c", which is labelled as t2.

In this case, the duty cycle in the first period becomes approximately 43.7% due to the truncation. The period (from the start of the first pulse to the start of the second pulse at t2) has also been modified (not depicted).

As the transmitted energy 1550*e* is low or approximately zero (from t1), the implantable device 100 uses/loses a portion of the stored energy 510*e*, so the energy storage level 510*e* goes down below the first energy storage protection level 511.

As the energy transmission device 1000 is configured and arranged to keep transmitting energy unless a modified sufficient energy signal 2566 is received, a second pulse 1550*e* is transmitted at t2 with substantially the same amplitude (power) 1551 as the previous first pulse—in other words, at a first amplitude (or power) level 1551. Because the energy storage level 510*e* is less than the first protection level 511, the implantable device 100 allows at least a portion of the energy received to charge the energy storage 510*e* and the level of the energy storage 510*e* rises upward.

At time t3, the energy storage level 510*e* again becomes the same as the first energy storage protection level 511. At that moment, the energy storage monitoring (not depicted) generates a further "a-type" modified sufficient energy signal 2566, which is transmitted as modified data-out 2566*o* from the implantable device 100 to the energy transmission device 1000. This modified sufficient energy signal "a-type" is a signal, signifying a request to pause.

The modified sufficient energy signal as modified data-out 2566*o* is detected by the energy transmission device 1000 and the energy transmission device 1000 takes suitable actions to immediately pause the transmission of energy 1550*e* through the one or more energy transmitters 1550*t*. As depicted, the energy transmission 1550*e* ends at t4.

Additionally, the energy transmission device 1000 recognizes the modified sufficient energy signal 2566 as a further "a-type"—the energy transmission device 1000 is configured and arranged to transmit the next pulse after pause duration "c".

In the example, the scheduled remaining duration (not depicted) of the pulse being transmitted 1550*e* is greater than the stopping time, so the pulse being transmitted 1550*e* will be truncated at t4, the truncated duration being less than the scheduled duration. The energy transmission device 1000 schedules the next pulse to be transmitted at t4+"c", which is labelled as t5.

In this case, the duty cycle in the second period becomes approximately 22.4% due to the truncation. The period (from the start of the second pulse at t2 to the start of the third pulse at t5) has also been modified (not depicted)—it is approximately 10% less than the first period.

As the transmitted energy 1550*e* is low or approximately zero (from t4, the implantable device 100 uses/loses a portion of the stored energy 510*e*, so the energy storage level 510*e* goes down below the first energy storage protection level 511.

As the energy transmission device 1000 is configured and arranged to keep transmitting energy unless a modified sufficient energy signal 2566 is received, a third pulse 1550*e* is transmitted at t5 with substantially the same amplitude (power) 1551 as the previous first and second pulses—in other words, at the first amplitude or power level 1551. Because the energy storage level 510*e* is less than the first protection level 511, the implantable device 100 allows at least a portion of the energy received to charge the energy storage module 510*m* and the level of the energy storage 510*e* rises upward. At time t6, the energy storage level 510*e* becomes the same as the first energy storage protection level 511. At that moment, the energy storage monitoring (not depicted) generates a "b-type" modified sufficient energy signal 2566, which is transmitted as modified data-out 2566*o* from the implantable device 100 to the external energy transmission device 1000. This modified sufficient energy signal "b-type" is a signal, signifying a request to pause.

The modified sufficient energy signal as modified data-out 2566*o* is detected by the energy transmission device 1000 and the energy transmission device 1000 takes suitable actions to immediately pause the transmission of energy 1550*e* through the one or more energy transmitters 1550*t*. As depicted, the energy transmission 1550*e* ends at t7.

Additionally, the energy transmission device 1000 recognizes the modified sufficient energy signal 2566 as a "b-type"—the energy transmission device 1000 is configured and arranged to transmit the next pulse after a longer-than-standard pause duration "d".

In the example, the scheduled remaining duration (not depicted) of the pulse being transmitted 1550*e* is greater than the stopping time, so the pulse being transmitted 1550*e* will be truncated at t7, the truncated duration being less than the scheduled duration. The energy transmission device 1000 schedules the next pulse to be transmitted at t7+"d", which is labelled as t8.

In this case, the duty cycle in the third period becomes approximately 20.6% due to the truncation. The period (from the start of the third pulse at t5 to the start of the fourth pulse at t8) has also been modified (not depicted)—it is approximately 17% longer than the second period, and approximately 6% longer than the first period.

As the transmitted energy 1550*e* is low or approximately zero (from t7, the implantable device 100 uses/loses a portion of the stored energy 510*e*, so the energy storage level 510*e* goes down below the first energy storage protection level 511.

As the energy transmission device 1000 is configured and arranged to keep transmitting energy unless a modified sufficient energy signal 2566 is received, a fourth pulse 1550*e* is transmitted at t8 with substantially the same amplitude (power) 1551 as the previous first, second and third pulses—in other words, at the first amplitude or power level 1551. Because the energy storage level 510*e* is less than the first protection level 511, the implantable device 100 allows at least a portion of the energy received to charge the energy storage module 510*m* and the level of the energy storage 510*e* rises upward.

At time t9, the energy storage level 510*e* becomes the same as the first energy storage protection level 511. At that moment, the energy storage monitoring (not depicted) generates a further "b-type" modified sufficient energy signal 2566, which is transmitted as modified data-out 2566*o* from the implantable device 100 to the external energy transmission device 1000. This modified sufficient energy signal "b-type" is a signal, signifying a request to pause.

The modified sufficient energy signal as modified data-out 2566*o* is detected by the energy transmission device 1000 and the energy transmission device 1000 takes suitable actions to immediately pause the transmission of energy 1550*e* through the one or more energy transmitters 1550*t*. As depicted, the energy transmission 1550*e* ends at t10.

Additionally, the energy transmission device 1000 recognizes the modified sufficient energy signal 2566 as a "b-type"—the energy transmission device 1000 is configured and arranged to transmit the next pulse after longer-than-standard pause duration "d".

In the example, the scheduled remaining duration (not depicted) of the pulse being transmitted 1550*e* is greater than the stopping time, so the pulse being transmitted 1550*e* will be truncated at t10, the truncated duration being less than the scheduled duration. The energy transmission device 1000 schedules the next pulse to be transmitted at t10+"d", which is not indicated.

In this case, the duty cycle in the fourth period becomes approximately 23.3% due to the truncation. The period (from the start of the fourth pulse at t8 to the start of the next pulse (not depicted) has also been modified (not depicted)—it is approximately 7% longer than the third period, approximately 26% longer than the second period, and approximately 14% longer than the first period.

Additionally or alternatively, a further communication channel may be provided between the energy transmission device 1000 and the implantable device 100. The implantable device 100 may be further configured and arranged to distinguish variations in one or more transmitted pulse 1550*e* parameters, such as duty cycle, period, the duration between received energy pulses (pause duration), and any combination thereof. Additionally or alternatively, the implantable device 100 may be further configured and arranged to measure one or more transmitted pulse 1550*e* parameters, such as duty cycle, period, the duration between received energy pulses (pause duration), and any combination thereof.

For example, if the energy transmission device 1000 is configured and arranged to modify one or more transmitted pulse 1550*e* parameters, such as the pause duration, communication may be provided from the energy transmission device 1000 to the implantable device 100 without significantly affecting normal operation.

For example, as depicted in the example of FIG. 10, two types of pause duration are depicted—a "c-type" standard pause duration between t1 and t2 and between t4 and t5, for example approx. 150 us (microseconds), and a "d-type" longer-than-standard pause duration between t7 and t8 and from t10, for example approx. 200 us (microseconds). Any number of variations in pause duration may be used that are distinguishable by the implantable device 100.

Optionally, the implantable device 100 may be further configured and arranged to determine whether a modified sufficient energy signal 2566 was transmitted immediately prior to the pause duration under consideration. In other words, agreement with expected behavior and/or deviation from expected behavior may also be distinguished.

Optionally, the implantable device 100 may further store, in a history database, one or more parameters from one or more previous operating cycles to allow comparison with one or more parameters determined and/or measured during the current operating cycle. Optionally, the history database may store one or more parameters from a plurality of energy transmission devices 1000.

As mentioned above, a simple encoding may be preferred in many configurations, although it may be configured and arranged to provide stimulation and treatment parameters, For example, in a simple encoding, a "c-type" pause duration may be considered as a "0" bit and a "d-type" pause duration as a "1" bit. This communication may be used to control, or provide feedback on, one or more parameters of the energy transmission, which includes:
  feedback regarding the quality of communication, feedback regarding one or more parameters associated with the received sufficient energy signals, additional data regarding one or more parameters associated with the transmitted energy pulses, additional data regarding previous/current/future transmissions, or any combination thereof.

Optionally, the energy transmission device 1000 may further store, in a history database, one or more parameters from one or more previous operating cycles to allow comparison with one or more parameters determined and/or measured during the current operating cycle. Optionally, the history database may store one or more parameters from a plurality of implantable devices 100.

For example, an energy transmission device 1000 may be further configured and arranged:
  to monitor one or more historic parameters associated with one or more transmitted energy pulses 1550*e;*
  to monitor the one or more historic parameters before the first and/or further sufficient energy signal 566, 2566 are received;
  to generate a monitor dataset comprising the one or more historic parameters;
  to generate a history database comprising a plurality of monitor datasets;
  to derive, from the history database, an expected amount of energy to be transmitted before a sufficient energy signal 566, 2566 is received;
  to compare a subsequent monitor dataset with the expected amount of energy to be transmitted; and
  identify a significant difference between the expected amount of energy to be transmitted and the subsequent monitor dataset.

This may be advantageous as one or more significant differences may indicate that the status of the implantable device 100 has changed, or is predicted to change—for example, that the implantable device 100 is defective, that a risk of defective operation is increased, that a risk of inefficient operation is increased, that an unexpected degree of ingress of fluid has occurred, that a primary and/or secondary energy source has an unwanted degree of depletion, or any combination thereof.

FIG. 5 and FIG. 6 depict examples of nerves that may be stimulated using a suitably configured implantable second substrate portion of the stimulator 100 to provide neurostimulation to treat, for example, headaches or primary headaches.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the portions of the device to be implanted, a suitable location may be determined to provide the electrical stimulation required for the treatment. Approximate implant locations for the distal end of stimulation devices 100 are depicted in FIG. 5 and FIG. 6 as regions:
  location 810 for left supraorbital stimulation and location 820 for right supraorbital stimulation for treating chronic headache such as migraine and cluster.
  location 830*a* or location 830*b* for left occipital stimulation and location 840*a* or location 840*b* for right occipital stimulation for treating chronic headache such as migraine, cluster, and occipital neuralgia.

In many cases, these will be the approximate locations 810, 820, 830*a/b*, 840*a/b* for the implantable stimulator 100.

For each implant location, 810, 820, 830*a/b*, 840*a/b* a separate stimulation system may be used. Where implant locations 810, 820, 830*a/b*, 840*a/b* are close together, or even overlapping, a single stimulation system may be configured to stimulate at more than one implant location 810, 820, 830*a/b*, 840*a/b* by increasing the length of the substrate 300 and/or the length of the portion with at least two electrodes 200, 400.

A plurality of stimulation devices 100, 103, 104, 105 may be operated separately, simultaneously, sequentially or any combination thereof to provide the required treatment.

FIG. 7 depicts further examples of nerves that may be stimulated using a suitably configured improved implantable stimulator 100 to provide neurostimulation to treat other conditions. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

location 810 for cortical stimulation for treating epilepsy;

location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery;

location 860 for vagus nerve stimulation for treating epilepsy, depression, anxiety, bulimia, obesity, tinnitus, obsessive compulsive disorder, heart failure, Crohn's disease, and rheumatoid arthritis;

location 860 for carotid artery or carotid sinus stimulation for treating hypertension;

location 860 for hypoglossal & phrenic nerve stimulation for treating sleep apnea;

location 865 for cerebral spinal cord stimulation for treating chronic neck pain;

location 870 for peripheral nerve stimulation for treating limb pain, migraines, extremity pain;

location 875 for spinal cord stimulation for treating chronic lower back pain, angina, asthma, pain in general;

location 880 for gastric stimulation for treatment of obesity, bulimia, interstitial cystitis;

location 885 for sacral & pudendal nerve stimulation for treatment of interstitial cystitis;

location 885 for sacral nerve stimulation for treatment of urinary incontinence, fecal incontinence;

location 890 for sacral neuromodulation for bladder control treatment; and location 895 for fibular nerve stimulation for treating gait or footdrop.

Other conditions that may be treated include gastroesophageal reflux disease, an autoimmune disorder, inflammatory bowel disease, and inflammatory diseases, among others.

Depending on the size of the region to be stimulated and the dimensions of the portions of the device to be implanted, a suitable location may be determined to provide the electrical stimulation required for the treatment.

For some treatments, stimulation of other tissue and/or indirect stimulation of nerves may be advantageous. For example, additionally or alternatively, the implantable device 100 may be configured and arranged to stimulate, in use, one or more muscles, one or more organs, spinal cord tissue, brain tissue, one or more cortical surface regions, one or more sulci, or any combination thereof.

For example, such additional or alternative stimulation may be performed at body locations which include suitable locations described above and/or depicted in FIG. 5, FIG. 6 and/or FIG. 7.

The descriptions thereof herein should not be understood to prescribe a fixed order of performing the method steps described therein. Rather the method steps may be performed in any order that is practicable. Similarly, the examples used to explain the methods are presented as non-limiting examples, and are not intended to represent the only implementations of these methods. The person skilled in the art will be able to conceive many different ways to achieve the same functionality as provided by the embodiments described herein.

For example, it may be advantageous for the implantable device 100 to comprise one or more signal transmitters, separate from the one or more energy receivers 550*r*, and configured and arranged to transmit signals (data) 520 to the external energy transmission device 1000. This is advantageous because it allows separate energy and signal (data) channels to be optimized separately. The one or more signal transmitters may be connected, for example, to the control module 503 using one or more interconnections 250.

Additionally or alternatively, one or more signal transmitters may be comprised within the pulse energy controller 500.

For example, it may be advantageous for the energy transmission device 1000 to comprise one or more signal receivers, separate from the one or more energy transmitters 1550*t*, and configured and arranged to receive signals (data) 520 from the implantable device 100. This is advantageous because it allows each separate energy and signal (data) channel to be optimized separately. The one or more signal receivers 1520 may be connected to the energy transmission controller 1500.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

For example:

one or more electrodes of the first type 200*a*, 200*b* are comprised in the first surface 310 and one or more electrodes of the second type 400*a*, 400*b* are comprised in the second surface 320; or one or more electrodes of the first type 200*a*, 200*b* are comprised in the first surface 310 and one or more electrodes of the second type 400*a*, 400*b* are also comprised in the first surface 310; or one or more electrodes of the first type 200*a*, 200*b* are comprised in the second surface 320 and one or more electrodes of the second type 400*a*, 400*b* are comprised in the first surface 310; or one or more electrodes of the first type 200*a*, 200*b* are comprised in the second surface 320 and one or more electrodes of the second type 400*a*, 400*b* are also comprised in the second surface 320; or any combination thereof.

Additionally, or alternatively, the substrate 300 and electrical components may be embedded in one or more flexible bio-compatible encapsulation layers. These layers may comprise: a Liquid Crystal Polymer (LCP), a Polydimethylsiloxane (PDMS), a silicone polyurethane, a Polyimide, a parylene, a biocompatible polymer, a biocompatible elastomer, and any combination thereof.

By providing relatively larger higher electrode 200, 400 surfaces, stimulator 100 may be operated at a lower energy/lower power usage. This may be advantageous in applications where high frequency and/or burst stimulation is used.

High frequency operation may require more energy to be provided by the pulse generator 500. In applications where energy/power is critical (for example, if an increased operating lifetime is desired from an energy source for electrical components, any reduction in required power may be advantageous. High frequency operation may be considered as generating electrical stimulation pulses with a frequency of 1000 Hz or more, 1500 Hz or more, 2000 Hz or more, 2500 Hz or more.

Experiments with burst stimulation have been performed such as Burst Occipital Nerve Stimulation for Chronic Migraine and Chronic Cluster Headache by Garcia-Ortega et al, Neuromodulation 2019; 22: 638-644, DOI: 10.1111/ner.12977.

For burst operation, the electrical components are further configured and arranged to generate electrical stimulation pulses in groups of stimulation pulses.

For example, groups (or bursts) of stimulation pulses may comprise 2 to 10 pulses, more preferably 2 to 5 stimulation pulses. Stimulation pulses in a group may have a repetition frequency of more than 500 Hz, typically 1000 Hz, or more. Groups may be repeated at more than 5 Hz, typically 40 Hz, or more.

As with high frequency operations, burst operation may require more energy to be provided by the electrical components, and any reduction in required energy may be advantageous.

Additionally, the speed of charge-balance recovery may also increase with a lower impedance. By using a relatively thin-foil substrate 300, stimulation between an electrode of the first type 200 comprised in one surface 310, 320 and an electrode of the second type 400 comprised in the other surface 310, 320, the current path in tissue is relatively short, reducing impedance.

Similarly, using a substrate 300, and stimulation between an electrode of the first type 200 comprised in one surface 310, 320 and an adjacent electrode of the second type 400 comprised in the same surface 310, 320, provide a relatively short path through tissue.

In general, an implantable device 100, suitable for performing the methods as disclosed herein of controlling wireless energy transfer from an energy transmission device 1000, comprises:
- one or more energy receivers 550r, configured and arranged to wirelessly receive a plurality of successive energy pulses 1550e, transmitted at a first power level 1551;
- an energy storage 510e, configured and arranged to store at least a portion of the energy received by the one or more energy receivers 550r;
- an energy monitor 530, configured and arranged to monitor a status level 530 of the energy storage 510e, wherein the status level 530 is significantly affected by energy received by the implantable device 100 and/or energy used by the implantable device 100; the implantable device 100 being further configured and arranged:
  - to create an energy transmission channel between the one or more energy receivers 550r and one or more energy transmitters 1550t comprised in the energy transmission device 1000; and
  - to transmit a first sufficient energy signal 566, 2566 if the status level 530 of energy storage 510e exceeds a first maximum value 511.

In general, an energy transmission device 1000, suitable for performing the methods as disclosed herein of controlling wireless energy transfer to a wireless implantable device 100, comprises:
- one or more energy transmitters 1550t, configured and arranged to wirelessly transmit a plurality of energy pulses 1550e at the first power level 1551; and
- one or more signal receivers 550r, configured to detect sufficient energy signals 566, 2566 from the implantable device 100;
- the energy transmission device 1000 being further configured and arranged:
  - to create an energy transmission channel between the one or more energy transmitters 1550t and one or more energy receivers 550r comprised in the wireless implantable device 100;
  - to pause energy pulse transmission 1550e immediately after the first sufficient energy signal 566, 2566 is received; and
  - to subsequently resume energy pulse transmission 1550e at the first power level 1551 if no further sufficient energy signal 566, 2566 is received.

Additionally or alternatively, an implantable device 100 may be configured to co-operate with a plurality of different energy transmission devices 1000. Additionally or alternatively, an energy transmission device 1000 may be configured to co-operate with a plurality of different implantable devices 100. Co-operation may be arranged by standardization and/or customization of one or more components.

Allowing more than one co-operating energy transmitting devices 1000 may allow a healthcare or cosmetic professional to operate an implantable device 100 in therapeutic, cosmetic, and/or experimental ways, and the human or animal may have their own energy transmitting device 1000 with more limited (everyday) functions.

Additionally or alternatively, the energy transmitting device 1000 may be comprised in a mobile device, such as a mobile telephone.

Optionally, an implantable device 100 may further comprise:
- a further energy storage (not depicted), configured and arranged to provide a significant amount of energy to one or more components during periods in which the energy received 550e by the energy receivers 550r is reduced.

This may be advantageous as it allows a small voltage to be applied, for example to logic, whereby the data stored and/or programmed is retained.

For example, the further energy storage may comprise one or more capacitors, one or more supercapacitors, one or more rechargeable batteries, one or more single use batteries (non-rechargeable), or any combination thereof.

The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application.

REFERENCE NUMERALS 100 implantable device, configured as an implantable stimulator
200ab one or more stimulation electrodes
250 one or more stimulation electrical interconnection layers
300 a substrate
310 a first surface of the substrate
320 a second surface of the substrate
400ab one or more return electrodes
401abcd one or more blocking capacitors
500 a pulse generator or pulse energy controller
501 an energy supply regulation module
502 a stimulation module
503 a control module
504 a wireless energy receiver module
505 a communications module
506 a micro controller
507 a current source
510m an energy storage module
510e energy stored
511 first energy storage protection level
512 second energy storage protection level 513 third energy storage protection level
514 energy storage—lower limit
515 energy storage—upper limit
520 one or more signal transmitters
530 an energy storage monitor
540 one or more tuning components, or tuner
545 one or more detuning components, or detuner
550r one or more energy receivers
550e energy received
555 one or more receiver attachment magnets
560 a demodulator
561d data decoder
561i data in channel
563m a clock recovery module
563s clock recovery signal
565 a modulator
566e data encoder
566o data-out
569 a coil voltage
570 a rectifier
571 a high voltage
575 a voltage regulator or shunt, such as one or more Zener diodes
577 a voltage converter, such as a DC/DC voltage converter
578 a logic voltage
580 a switch controller
585abcd one or more switching units
600 a longitudinal axis
610 a first substrate portion or a proximal end
620 a second substrate portion or a distal end
700 a first transverse axis
750 a second transverse axis
800 median plane of subject
810 location for left supraorbital nerve or cortical stimulation
820 location for right supraorbital nerve or cortical stimulation
830a first location for left occipital nerve stimulation
830b second location for left occipital nerve stimulation
840a first location for right occipital nerve stimulation
840b second location for right occipital nerve stimulation
850 location for deep brain stimulation
860 location for vagus nerve, carotid artery, carotid sinus, phrenic nerve or
hypoglossal stimulation
865 location for cerebral spinal cord stimulation
870 location for peripheral nerve stimulation
875 location for spinal cord stimulation
880 location for gastric stimulation
885 location for sacral & pudendal nerve stimulation
890 location for sacral neuromodulation
895 location for fibular nerve stimulation
910 left supraorbital nerve
920 right supraorbital nerve
930 left greater occipital nerve
940 right greater occipital nerve
1000 an external energy transmission device
1500 an energy transmission controller
1501 an energy supply regulator
1503 a control module
1504 a wireless energy transmitter module
1505 a communications module
1510 an energy storage module
1520 one or more signal receivers
1550t one or more energy transmitters
1550e transmitted energy
1551 a first amplitude or power level
1552 an initial amplitude or power level
1553 a significantly reduced amplitude or power level
1555 one or more transmitter attachment magnets
2566o modified data-out

The invention claimed is:

1. A method of controlling wireless energy transfer from an energy transmission device to a wireless implantable device, the implantable device comprising:
  one or more energy receivers to wirelessly receive a plurality of successive energy pulses, transmitted at a first power level;
  an energy storage to store at least a portion of the energy received by the one or more energy receivers; and
  an energy monitor to monitor a status level of the energy storage, wherein the status level is significantly affected by energy received by the implantable device and/or energy used by the implantable device;
the energy transmission device comprising:
  one or more energy transmitters to wirelessly transmit a plurality of energy pulses at the first power level; and
  one or more signal receivers to detect sufficient energy signals from the implantable device;
the method comprising:
  the energy transmission device starting energy pulse transmission at the first power level;
  the energy transmission device and the implantable device creating an energy transmission channel between the one or more energy transmitters and the one or more energy receivers;
  an energy receiver module in the implantable device transmitting a first sufficient energy signal when the status level of energy storage exceeds a first maximum value;
  the energy transmission device pausing energy pulse transmission immediately after the first sufficient energy signal is received; and
  subsequently resuming energy pulse transmission at the first power level when no further sufficient energy signal is received.

2. The method according to claim 1, further comprising:
  the implantable device transmitting the first and/or further sufficient energy signal by modifying one or more parameters of the energy transmission channel, whereby the modification of the one or more parameters is detectable by the energy transmission device.

3. The method according to claim 2, wherein the implantable device modifies the tuning of the energy transmission channel to transmit as load-shift keying (LSK).

4. The method according to claim 1, wherein the implantable device:
  provides a degree of detuning of the energy transmission channel when the energy storage status level exceeds a second maximum value.

5. The method according to claim 1, wherein the implantable device further comprises one or more voltage regulators controlling at least a portion of the energy stored in the energy storage, the method further comprising:
  the implantable device reducing the output voltage of the voltage regulator when the energy storage status level exceeds a third maximum value.

6. The method according to claim 1, wherein the implantable device further comprises one or more shunts for reducing at least a portion of the energy stored in the energy storage, the method further comprising:
  the implantable device operating the one or more shunts when the energy storage status level exceeds a third maximum value.

7. The method of claim 1, wherein the energy storage comprises at least one of one or more capacitors and one or more supercapacitors.

8. The method of claim 1, wherein the energy storage comprises no batteries.

9. The method of claim 1, wherein the implantable device further comprises:
a further energy storage to provide a significant amount of energy to one or more components during periods in which the energy received by the energy receivers is reduced.

10. The method of claim 9, wherein the further energy storage comprises at least one of one or more capacitors, one or more supercapacitors, one or more rechargeable batteries, and one or more single use batteries.

11. The method according to claim 1, wherein the implantable device is configured and arranged:
to transmit sufficient energy signals centered around two or more modulation frequencies; and
to select the central modulation frequency of the first and/or further sufficient energy signals.

12. The method according to claim 11, wherein the implantable device is configured and arranged to transmit sufficient energy signals centered around two modulation frequencies.

13. The method according to claim 12, wherein the implantable device is configured and arranged to transmit sufficient energy signals centered around approximately 212 kHz and approximately 424 kHz.

14. The method according to claim 11, wherein the one or more signal receivers comprised in the energy transmission device are configured to detect two or more center modulation frequencies of the first and/or further sufficient energy signals.

15. The method according to claim 14, wherein the energy transmission device is configured and arranged to modify one or more parameters of the energy pulse transmission based on one or more center modulation frequencies of the first and/or further sufficient energy signals.

16. The method according to claim 15, wherein the one or more parameters include at least one of: a duration of one or more energy transmission pulses, a period between two or more energy transmission pulses, and the first power level of a plurality of energy transmission pulses.

17. The method of claim 1, wherein the implantable device further comprises:
a pulse generator to receive electrical energy from the energy storage for its operation, and to generate at least one stimulation pulse;
at least two electrodes; and
a plurality of electrical interconnections, electrically coupling the pulse generator to the at least two electrodes;
the method further comprising:
configuring and arranging the pulse generator to provide electrical stimulation energy to the at least two electrodes as one or more electrical treatment stimulation pulses.

18. The method of claim 17, wherein the at least two electrodes are configurable, using one or more parameters of the pulse generator, as a stimulation electrode or a return electrode.

19. The method of claim 17, wherein the pulse generator comprises the one or more energy receivers.

20. The method of claim 17, wherein the implantable device further comprises:
a substrate, the substrate comprising a first and second surface, wherein a thickness of the substrate is defined by the first and second surfaces;
wherein:
the at least two electrodes are comprised in an electrode array located along a conformable portion of the substrate;
the plurality of electrical interconnections are positioned between the first and second surfaces of the substrate; and
the thickness of the substrate along the conformable portion is equal to or less than 0.5 millimeters.

21. The method according to claim 20, wherein the conformable portion of the substrate comprises at least one of a polymer and a Liquid Crystal Polymer (LCP).

22. The method according to claim 17, wherein the substrate comprises a further portion along which the pulse generator is located, the implantable device further comprising an encapsulation layer at least partially covering the further portion of the substrate.

23. The method according to claim 22, wherein the encapsulation layer comprises at least one of a polymer, a Polydimethylsiloxane (PDMS), a silicone polyurethane, a Polyimide, a parylene, a biocompatible polymer, and a biocompatible elastomer.

24. The method according to claim 17, wherein the implantable device is configured and arranged to stimulate, in use, at least one of one or more nerves, one or more muscles, one or more organs, spinal cord tissue, brain tissue, one or more cortical surface regions, and one or more sulci.

25. The method according to claim 17, wherein the implantable device is configured and arranged to treat at least one of headaches, chronic headaches, primary headaches, dystonia, obsessive compulsive disorder, anxiety, depression, sleep disorders, autism, bipolar, stroke recovery, incontinence, bladder control, occipital neuralgia, sleep apnea, hypertension, angina, asthma, heart failure, gastroesophageal reflux disease, bulimia, tinnitus, traumatic brain injury, an inflammatory disease, limb pain, leg pain, back pain, lower back pain, phantom pain, chronic pain, epilepsy, essential tremor, an overactive bladder, gait, footdrop, post-stroke pain, obesity, interstitial cystitis, an autoimmune disorder, rheumatoid arthritis, inflammatory bowel disease, Crohn's disease, Parkinson's disease, Tourette's, and Alzheimer's.

26. The method according to claim 1, wherein the energy receiver module comprises a modulator that transmits the first sufficient energy signal.

27. The method according to claim 1, wherein the implantable device further comprises a voltage regulator and a shunt, wherein the voltage regulator and the shunt are configured to reduce a voltage when an energy storage protection value is exceeded.

28. The method according to claim 1, wherein the implantable device is configured to transmit an instruction to the energy transmission device such that subsequent energy pulse transmissions are reduced in intensity when compared to the energy pulse transmission at the first power level.

29. A method of controlling wireless energy transfer from an energy transmission device to a wireless implantable device, the implantable device comprising:
one or more energy receivers to wirelessly receive a plurality of successive energy pulses, transmitted at a first power level;
an energy storage to store at least a portion of the energy received by the one or more energy receivers; and an energy monitor to monitor a status level of the energy storage, wherein the status level is significantly affected by energy received by the implantable device and/or energy used by the implantable device;

the energy transmission device comprising:

one or more energy transmitters to wirelessly transmit a plurality of energy pulses at the first power level; and one or more signal receivers to detect sufficient energy signals from the implantable device;

the method comprising:

the energy transmission device starting energy pulse transmission at the first power level;

the energy transmission device and the implantable device creating an energy transmission channel between the one or more energy transmitters and the one or more energy receivers;

an energy receiver module in the implantable device transmitting a first sufficient energy signal when the status level of energy storage exceeds a first maximum value;

the energy transmission device pausing energy pulse transmission immediately after the first sufficient energy signal is received;

subsequently resuming energy pulse transmission at the first power level when no further sufficient energy signal is received; and the energy transmission device pausing energy pulse transmission within two milliseconds or less, within one millisecond or less, within 100 microseconds or less, or within 10 microseconds or less, after the first or further sufficient energy signal is received.

30. A method of controlling wireless energy transfer from an energy transmission device to a wireless implantable device, the implantable device comprising:

one or more energy receivers to wirelessly receive a plurality of successive energy pulses, transmitted at a first power level;

an energy storage to store at least a portion of the energy received by the one or more energy receivers; and an energy monitor to monitor a status level of the energy storage, wherein the status level is significantly affected by energy received by the implantable device and/or energy used by the implantable device;

the energy transmission device comprising:

one or more energy transmitters to wirelessly transmit a plurality of energy pulses at the first power level; and one or more signal receivers to detect sufficient energy signals from the implantable device;

the method comprising:

the energy transmission device starting energy pulse transmission at the first power level;

the energy transmission device and the implantable device creating an energy transmission channel between the one or more energy transmitters and the one or more energy receivers;

an energy receiver module in the implantable device transmitting a first sufficient energy signal when the status level of energy storage exceeds a first maximum value;

the energy transmission device pausing energy pulse transmission immediately after the first sufficient energy signal is received; and subsequently resuming energy pulse transmission at the first power level when no further sufficient energy signal is received, wherein the energy storage provides sufficient energy to operate the implantable device, wherein the duration of the pause in energy pulse transmission is 1000 milliseconds or less, 500 milliseconds or less, 200 milliseconds or less, 100 milliseconds or less, 50 milliseconds or less, 20 milliseconds or less, or 10 milliseconds or less.

31. A method of controlling wireless energy transfer from an energy transmission device to a wireless implantable device, the implantable device comprising:

one or more energy receivers to wirelessly receive a plurality of successive energy pulses, transmitted at a first power level;

an energy storage to store at least a portion of the energy received by the one or more energy receivers; and an energy monitor to monitor a status level of the energy storage, wherein the status level is significantly affected by energy received by the implantable device and/or energy used by the implantable device;

the energy transmission device comprising:

one or more energy transmitters to wirelessly transmit a plurality of energy pulses at the first power level; and one or more signal receivers to detect sufficient energy signals from the implantable device;

the method comprising:

the energy transmission device starting energy pulse transmission at the first power level;

the energy transmission device and the implantable device creating an energy transmission channel between the one or more energy transmitters and the one or more energy receivers;

an energy receiver module in the implantable device transmitting a first sufficient energy signal when the status level of energy storage exceeds a first maximum value;

the energy transmission device pausing energy pulse transmission immediately after the first sufficient energy signal is received;

subsequently resuming energy pulse transmission at the first power level when no further sufficient energy signal is received;

predetermining and/or controlling the energy transmission device to transmit energy pulses with a first duration;

the energy transmission device starting the transmission of a first pulse with the first duration;

the energy transmission device receiving the first or further sufficient energy signal; and the energy transmission device pausing energy pulse transmission, whereby the first pulse is truncated such that the first pulse has a truncated duration that is shorter than the first duration.

32. A method of controlling wireless energy transfer from an energy transmission device to a wireless implantable device, the implantable device comprising:

one or more energy receivers to wirelessly receive a plurality of successive energy pulses, transmitted at a first power level;

an energy storage to store at least a portion of the energy received by the one or more energy receivers; and an energy monitor to monitor a status level of the energy storage, wherein the status level is significantly affected by energy received by the implantable device and/or energy used by the implantable device;

the energy transmission device comprising:

one or more energy transmitters to wirelessly transmit a plurality of energy pulses at the first power level; and one or more signal receivers to detect sufficient energy signals from the implantable device;

the method comprising:

the energy transmission device starting energy pulse transmission at the first power level;

the energy transmission device and the implantable device creating an energy transmission channel between the one or more energy transmitters and the one or more energy receivers;

an energy receiver module in the implantable device transmitting a first sufficient energy signal when the status level of energy storage exceeds a first maximum value;

the energy transmission device pausing energy pulse transmission immediately after the first sufficient energy signal is received; and subsequently resuming energy pulse transmission at the first power level when no further sufficient energy signal is received;

wherein the energy transmission device:

monitors one or more historic parameters associated with one or more transmitted energy pulses;

monitors the one or more historic parameters before the first and/or further sufficient energy signal are received;

generates a monitor dataset comprising one or more historic parameters;

generates a history database comprising a plurality of monitor datasets;

derives, from the history database, an expected amount of energy to be transmitted before a sufficient energy signal is received;

compares a subsequent monitor dataset with the expected amount of energy to be transmitted; and identifies a significant difference between the expected amount of energy to be transmitted and the subsequent monitor dataset.

33. A method, comprising:

transmitting, by an energy transmission device, at least one energy pulse at a first power level;

creating an energy transmission channel between the energy transmission device and a wireless implantable device between at least one energy transmitter and at least one energy receiver;

transmitting, by the wireless implantable device, a first energy signal when a status level of energy storage exceeds a first maximum value;

pausing, by the energy transmission device, the transmitting of the at least one energy pulse when the status level of the energy storage exceeds the first maximum value; and subsequently resuming energy pulse transmission at the first power level when no further sufficient energy signal is received.

* * * * *